(12) United States Patent
Koch et al.

(10) Patent No.: US 10,912,767 B2
(45) Date of Patent: Feb. 9, 2021

(54) ANTHRACYCLINE PRODRUGS AND METHODS OF MAKING AND USING THE SAME

(71) Applicant: THE REGENTS OF THE UNIVERSITY OF COLORADO, Denver, CO (US)

(72) Inventors: Tad H. Koch, Boulder, CO (US); Benjamin L. Barthel, Broomfield, CO (US); Hang Hubert Yin, Boulder, CO (US); Ryo Tamura, Boulder, CO (US); Alla Balabanova, Centennial, CO (US)

(73) Assignee: THE REGENTS OF THE UNIVERSITY OF COLORADO, A BODY CORPORATE, Denver, CO (US)

( * ) Notice: Subject to any disclaimer, the term of this patent is extended or adjusted under 35 U.S.C. 154(b) by 0 days.

(21) Appl. No.: 15/564,773

(22) PCT Filed: Apr. 27, 2016

(86) PCT No.: PCT/US2016/029575
§ 371 (c)(1),
(2) Date: Oct. 6, 2017

(87) PCT Pub. No.: WO2016/176332
PCT Pub. Date: Nov. 3, 2016

(65) Prior Publication Data
US 2018/0110756 A1 Apr. 26, 2018

Related U.S. Application Data

(60) Provisional application No. 62/153,320, filed on Apr. 27, 2015.

(51) Int. Cl.
| | | |
|---|---|---|
| *A61K 31/424* | (2006.01) | |
| *A61K 31/337* | (2006.01) | |
| *A61K 31/704* | (2006.01) | |
| *A61K 31/573* | (2006.01) | |
| *A61K 31/675* | (2006.01) | |
| *A61K 31/475* | (2006.01) | |
| *A61P 35/00* | (2006.01) | |
| *A61K 31/7056* | (2006.01) | |
| *A61K 45/06* | (2006.01) | |

(52) U.S. Cl.
CPC .......... *A61K 31/424* (2013.01); *A61K 31/337* (2013.01); *A61K 31/475* (2013.01); *A61K 31/573* (2013.01); *A61K 31/675* (2013.01); *A61K 31/704* (2013.01); *A61K 31/7056* (2013.01); *A61K 45/06* (2013.01); *A61P 35/00* (2018.01); *A61K 2300/00* (2013.01)

(58) Field of Classification Search
CPC ..... A61P 35/00; A61K 31/704; A61K 31/424; A61K 45/06; A61K 31/7056; A61K 31/675; A61K 31/573; A61K 31/475; A61K 31/337
See application file for complete search history.

(56) References Cited

U.S. PATENT DOCUMENTS

| | | | | |
|---|---|---|---|---|
| 7,282,567 | B2* | 10/2007 | Goldenberg | ....... A61K 49/0008 424/134.1 |
| 8,404,650 | B2* | 3/2013 | Koch | ................... A61K 31/704 514/25 |
| 8,491,896 | B2* | 7/2013 | Goldenberg | ....... A61K 51/0406 424/133.1 |
| 8,574,854 | B2* | 11/2013 | Gold | ................... A61K 51/0406 435/7.1 |
| 8,795,662 | B2* | 8/2014 | Gold | ................... A61K 51/0406 424/130.1 |
| 9,238,081 | B2* | 1/2016 | Gold | ................ A61K 47/48746 |

FOREIGN PATENT DOCUMENTS

| | | |
|---|---|---|
| WO | WO 00/26223 | 5/2000 |
| WO | WO 2007/102888 | 9/2007 |
| WO | WO 2008/029294 | 3/2008 |
| WO | WO 2014/165506 | 10/2014 |

OTHER PUBLICATIONS (R) Post et al. "Doxazolidine, a Proposed Active Metabolite of Doxorubciin that Cross-links DNA," Journal of Medicinal Chemisty, 48(24), 7648-7657 (Nov. 4, 2005).*
Intenational Preliminary Report on Patentability for International (PCT) Patent Application No. PCT/US2016/029575, dated Nov. 9, 2017 6 pages.
International Search Report for International Patent Application No. PCT/US2016/029575, dated Aug. 16. 2016, 4 pages.
Written Opinion for International Patent Application No. PCT/US2016/029575, dated Aug. 16, 2016, 4 pages.

* cited by examiner

*Primary Examiner* — Lawrence E Crane
(74) *Attorney, Agent, or Firm* — Berg Hill Greenleaf Ruscitti, LLP

(57) ABSTRACT

The present invention includes compounds of the class anthracycline that have been modified to include photo-activated prodrug anthracycline compounds that are useful in the treatment of cancer. One example composition of the invention may include photodoxazolidine which may be synthesized in two steps from 4,5-dimethoxy-2-nitrobenzyl alcohol and doxazolidine. In this embodiment commercial 4,5-dimethoxyl-2-nitrobenzyl alcohol reacts with p-nitrophenylchloroformate to give the p-nitrophenyl carbonate of the benzyl alcohol derivative. The p-nitrophenyl carbonate is then reacted with doxazolidine to give the exemplary photodoxazolidine composition.

6 Claims, 13 Drawing Sheets

Specification includes a Sequence Listing.

ANTHRACYCLINE PRODRUGS AND METHODS OF MAKING AND USING THE SAME

CROSS REFERENCE TO RELATED APPLICATION

This application is a national stage application under 35 U.S.C. 371 of PCT Application No. PCT/US2016/029575 having an international filing date of Apr. 27, 2016, which designated the United States, which PCT application claimed the benefit of U.S. Application Ser. No. 62/153,320, filed Apr. 27, 2015, both of which are incorporated by reference in their entirety.

GOVERNMENT INTEREST

This invention was made with government support under grant numbers R21CA141101, R21 CA143549 and R01 GM103843 awarded by the National Institutes of Health. The U.S. government has certain rights in the invention.

TECHNICAL FIELD

The disclosure provides anthracycline anti-tumor compounds and method of treating cancer using these compounds. Specifically, the disclosure provides photo-activated prodrug anti-cancer compounds having greater efficacy than doxorubicin and methods of synthesizing and using these anti-cancer compounds in the treatment of patients with cancer.

BACKGROUND OF DISCLOSURE

Doxorubicin is a broad-spectrum anthracycline, anti-tumor drug used for the treatment of leukemias, lymphomas and solid tumors and is a main-line drug for the treatment of breast cancer. Unfortunately, doxorubicin exhibits frequent and dose-limiting or drug-limiting cardiotoxicity. Additionally, most multidrug-resistant tumors and cancer cells display resistance to doxorubicin. While these undesirable characteristics have limited the clinical usefulness of doxorubicin, the drug remains one of the oldest and most used anthracycline anti-tumor compounds due to its substantial toxicity to sensitive cancer cells. For this reason, there has been an intensive search for similar anthracycline compounds or derivatives of doxorubicin having the same or similar anti-tumor activity with greater specificity and/or activity in drug-resistant neoplastic cells.

Research into the mechanism of action of doxorubicin led to the discovery of the potent formaldehyde doxorubicin derivative, Doxoform (DoxF; U.S. Pat. No. 6,677,309) which cross-links nuclear and mitochondrial DNA and inhibits equally the growth of sensitive and multidrug-resistant cancer cells. DoxF has shown substantial anti-tumor activity (approximately 100-fold above doxorubicin) that is attributable to the oxazolidine ring formed by the reaction of doxorubicin with formaldehyde. Unfortunately, DoxF is highly susceptible to hydrolysis and therefore, relatively unstable.

The anthracycline anti-cancer drug doxazolidine is a formaldehyde-adduct of the clinically used chemotherapeutic, doxorubicin, which exhibits increased potency, orders of magnitude greater than doxorubicin, due to a change in the drug's mechanism of action. However, under physiological conditions, doxazolidine undergoes rapid hydrolysis to the parent drug and formaldehyde, which prevents direct administration in vivo and instead

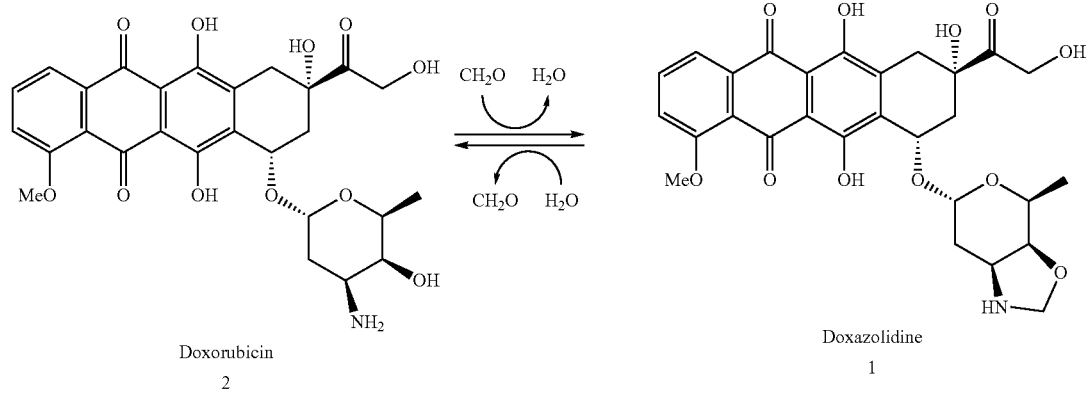

Doxorubicin
2

Doxazolidine
1 requires the use of a prodrug strategy.

Therefore, there is a need for improved anti-cancer prodrug compounds based on the widely used but highly toxic doxorubicin molecule that are effective, shelf stable and easily administered with improved cancer-targeting activities. Preferably, such anti-cancer compounds possess at least the anti-cancer efficacy of doxorubicin while eliminating, or substantially reducing, the associated cardiotoxicity and simultaneously overcoming the doxorubicin drug resistance displayed by many cancer cells. The foregoing disadvantages of the prior art anticancer compounds are overcome by the compounds and methods of this disclosure. Additionally, the compounds and methods of this disclosure achieve other advantages discussed more fully below.

SUMMARY

The present disclosure provides novel anticancer compounds, pharmaceutical compositions containing these compounds, as well as methods of making and using these novel compounds.

To design improved anti-cancer prodrug compounds based on the highly toxic doxorubicin molecule that are effective, shelf stable, easily administered, and with improved cancer-targeting activities, the inventors utilized a photoactivation strategy that can activate a cytotoxic prodrug inside or near a cancer cell, and/or cells involved in the angiogenesis of the cancer cell. Important design criteria are selective delivery of photons of sufficient energy for the activation and the release of a highly cytotoxic drug that is relatively short lived. As described above, the clinical antitumor drug doxorubicin reacts reversibly with formaldehyde at the vicinal amino alcohol to give doxazolidine, which is at least an order of magnitude more toxic to both sensitive and resistant cancer cells than doxorubicin, and its toxicity stems from a different mechanism (doxorubicin is a topoisomerase 2 poison, leading to DNA double strand breaks; doxazolidine crosslinks DNA to induce cell death). However, due to aqueous instability, efficacious in vivo use of doxazolidine requires delivery as a prodrug where activation occurs at the site of the tumor. Thus, doxazolidine is an ideal candidate for prodrug release as it is short-lived and highly toxic (at 37° C. and pH 7.4, doxazolidine has a half-life of 3 min, during which the oxazolidine ring hydrolyzes, reforming doxorubicin).

With the goal of developing a broad spectrum photoactivated prodrug for the treatment of cancer that releases a highly cytotoxic but short-lived compound at the site of metastatic tumors and/or their associated angiogenesis, the challenge is providing selective delivery of relatively high energy photons to which the body is not transparent. The inventors have designed photoactivated prodrugs of doxazolidine including a photoactive protecting group, ortho-nitrobenzyl, that may be photocleaved with near UV light at wavelengths 320-400 nm. Photoactivation of these prodrugs may be accomplished by the application of near UV light or from Cherenkov radiation that may be produced during a PET scan or simply with the radioactive material used in a PET scan. This activating radiation may be enhanced in the presence of $^{18}$F-2-deoxyglucose (18-FDG). 18-FDG is selective for tumor cells in vivo because of their high utilization of glucose as an energy source. Decay of the 18-FDG by positron emission gives rise to gamma rays useful for PET scans as well as Cherenkov radiation in the visible and near UV. Thus, photoactivation of the prodrugs of this disclosure may result from internal Cherenkov UV radiation produced during a PET scan in conjunction with 18-F-deoxyglucose (18-FDG), which may be administered to a subject and localize to a tumor cell in vivo prior to the PET scan.

Selective targeting of the compounds of this disclosure to a tumor site may not be required if enough drug accumulates at the tumors, but additional design/chemical features of the compounds of this disclosure may include tumor-selective targeting moieties. Thus, additional compounds of this disclosure include a prodrug of doxazolidine bearing a peptide targeting group attached to a photochemical cleavable tether.

Glucose is used as a targeting group in this invention, linked to the prodrugs of this disclosure through a photochemical cleavable tether. Glucose-conjugated photodoxazolidines target glucose transporters, which are overexpressed on the plasma membrane of cancer cells, and involved in the increased level of glucose uptake of cancer cells, including the uptake of 18-F-deoxyglucose.

Another targeting group utilized in this invention is a peptide referred to as the "MARCKS" peptides that bind to exosomes (Morton, et al., ACS Chem. Biol. 2013, 8: 218-25) on the surface of, and abundantly released from, some cancer cells that are thought to possess autocrine, paracrine, and/or endocrine communicative capacity via membrane fusion and delivery of their contents. A MARCKS targeting peptide (herein after "MARCKS-ED" having the sequence KKKKKRFSFKKSFKLSGFSFKKNKK (SEQ ID NO: 1) locates the prodrug on exosomes associated with cancer cells or in the blood stream. Exosomes in the blood stream should lodge in the leaky vasculature of metastatic tumors.

Thus, these exosome-targeted prodrugs of this disclosure may treat metastatic cancer even at metastases too small to be detected by a PET scan. All that is required is for 18-fluoroglucose, or related radioactive material, to find the metastases first, and thereafter photodoxazolidine, or targeted photodoxazolidine, prodrugs find the metastases. Cherenkov radiation, which may be supplied by positron emission, thereafter activates therapeutic amounts of the photodoxazolidine. While a PET scan may be expensive, the patient may need multiple treatments, but an actual PET scan may not be needed with each treatment. Additional MARCKS targeting peptides that are useful in the prodrug compounds of this disclosure include truncated versions of the MARCKS-ED peptide, KKKKKRFSFKK (SEQ ID NO:2) and SFKLSGFSFKKNKK (SEQ ID NO:3), as well as arginine and lysine peptide strings (believed to possess substantial targeting effects of the MARCKS peptides), RRRRRRRRRR (SEQ ID NO:4), and KKKKKKKKKK (SEQ ID NO:5). The amino acids of these sequences (SEQ ID NOs: 1-5) may be of the D or L configuration because binding to plasma membrane of tumor cells and of tumor cell exosomes stems, at least in part, from charge interaction of the positively-charged K or R residues with the negative charge of the abundant phosphatidyl serine residues on the outside of the membranes of cancer cells and cancer cell exosomes.

The prodrugs of this disclosure are highly attractive anti-cancer agents because doxazolidine is highly toxic but has the short in vivo half-life, as described above. Hence, doxazolidine that escapes the site of activation will be short lived relative to its hydrolysis to doxorubicin which is 1 to 3 orders of magnitude less toxic. If insufficient prodrug accumulates at the tumors, targeting moieties may be included in these prodrugs to further limit cellular toxicity to non-cancerous cells. Examples of targeted photodoxazolidine described here include MARCKS-PEG-Photodoxazolidine targeted to tumor cell exosomes and Glucose-PEG-Photodoxazolidine and Glucose-Photodoxazolidine targeted to tumor cell glucose transporters. Other targeting strategies will be apparent to those skilled in the art.

Thus, this disclosure provides photo-activated prodrugs of doxorubicin-formaldehyde conjugates, useful for treating cancer or inhibiting the growth of cancer cells in a subject. The compounds of this disclosure are selected from: Photodoxazolidine, Azido-PEG-Photodoxazolidine, MARCKS-PEG-Photodoxazolidine, Glucose-PEG-Photodoxazolidine, and Glucose-Photodoxazolidine. The chemical structures of these compounds are set forth below.

This disclosure also provides pharmaceutical compositions containing at least one compound of this disclosure, and at least one pharmaceutical excipient.

Another aspect of this disclosure provides methods of treating cancer, or other proliferative diseases, or ameliorating the symptoms of these diseases, by administering a therapeutically effective amount of at least one compound of this disclosure, or a pharmaceutically acceptable salt form thereof, to a subject in need of such treatment or suspected of having a cancer, or other proliferative disease.

An embodiment of this disclosure provides a method of treating cancer, or other proliferative disease, or ameliorating a symptom thereof, by administering a therapeutically effective amount of at least one of the compounds of this disclosure to a subject, and exposing the subject to Cherenkov radiation. The Cherenkov radiation may be provided to the subject by exposing the subject to a PET scan. The Cherenkov radiation and the therapeutically effective amount of at least one compound of this disclosure may be administered in conjunction with 18-F-deoxyglucose (18-FDG).

An embodiment of this disclosure provides a method of treating cancer, or other proliferative disease, or ameliorating a symptom thereof, by administering a therapeutically-effective combination of at least one of the compounds of this disclosure, and one or more other drugs. In example embodiments, the other drugs may include known anti-cancer or anti-proliferative compounds. For example, the other anti-cancer compounds may include at least one of irinotecan, adriamycin, cyclophosphamide, taxotere, bleomycin, vinblastine, dacarbazine, vincristine, prednisone, 5-fluorouracil, trastuzumab, taxol, docetaxel, ifosfamide, 6-mercaptopurine, gemcitabine, carvedilol, and topotecan.

Another embodiment of this disclosure is a method of treating cancer or other proliferative diseases, or ameliorating a symptom thereof, by administering a therapeutically effective amount of one of the compounds of the disclosure in conjunction with medically supervised radiation therapy, surgery, other forms of chemotherapy, immunotherapy, or combinations thereof.

In these embodiments, the cancer treated may include leukemia, lymphomas and solid tumors. More particularly, the cancer may be a cancer selected from breast, ovarian, colon, epidermoid, liver, pancreas, prostate, pancreatic, leukemia, small cell lung, cervical, neuroblastoma, endometrial, melanoma, renal and peritoneal cancers. In a specific embodiment, the cancer may be breast cancer. In another specific embodiment, the cancer may be ovarian cancer.

This disclosure also provides pharmaceutical compositions containing one or more of the compounds of the disclosure admixed with at least one pharmaceutically-acceptable carrier. Thus, in one aspect of the disclosure, a pharmaceutical composition of the disclosure, which contains at least one compound of the disclosure, is administered to a subject in need of such treatment.

Also provided herein are methods of treating or reducing the incidence of cancer in a subject, by administering to a subject in need thereof, therapeutically-effective amounts of any of the pharmaceutical compositions of the disclosure.

Also provided herein are packages containing a pharmaceutical composition comprising therapeutically-effective amounts of at least one compound of the disclosure, together with at least one pharmaceutically acceptable carrier. The pharmaceutical compositions may be administered separately, simultaneously or sequentially, with other compounds or therapies used in the prevention, treatment or amelioration of cancer. These packages may also include prescribing information and/or a container. If present, the prescribing information may describe the administration, and/or use of these pharmaceutical compositions alone, or in combination with activating light or radiation, or other therapies used in the prevention, treatment or amelioration of cancer.

This Summary is neither intended nor should it be construed as being representative of the full extent and scope of the present invention. Moreover, references made herein to "the present disclosure," or aspects thereof, should be understood to mean embodiments of the present invention and should not necessarily be construed as limiting all embodiments to a particular description. Additional aspects of the present disclosure will become more readily apparent from the Description of Embodiments, particularly when taken together with the drawings.

BRIEF DESCRIPTION OF DRAWINGS

FIG. 6A depicts steps in the synthesis of compound (1) through compound (5). FIG. 6B depicts steps in the synthesis of compound (6). FIG. 6C depicts steps in the synthesis of compound (7). FIG. 6D depicts steps in the synthesis of compound (9), MARCKS-PEG-Photodoxazolidine, which includes a covalent attachment to the MARCKS-ED peptide (KKKKKRFSFKKSFKLSGFSFKKNKK; SEQ ID NO:1)

FIG. 7A depicts steps in the synthesis of compound (11). FIG. 7B depicts the synthesis of compound (12), glucose-PEG-photodoxazolidine, from compound (11).

DESCRIPTION OF EMBODIMENTS

Figure 1A:
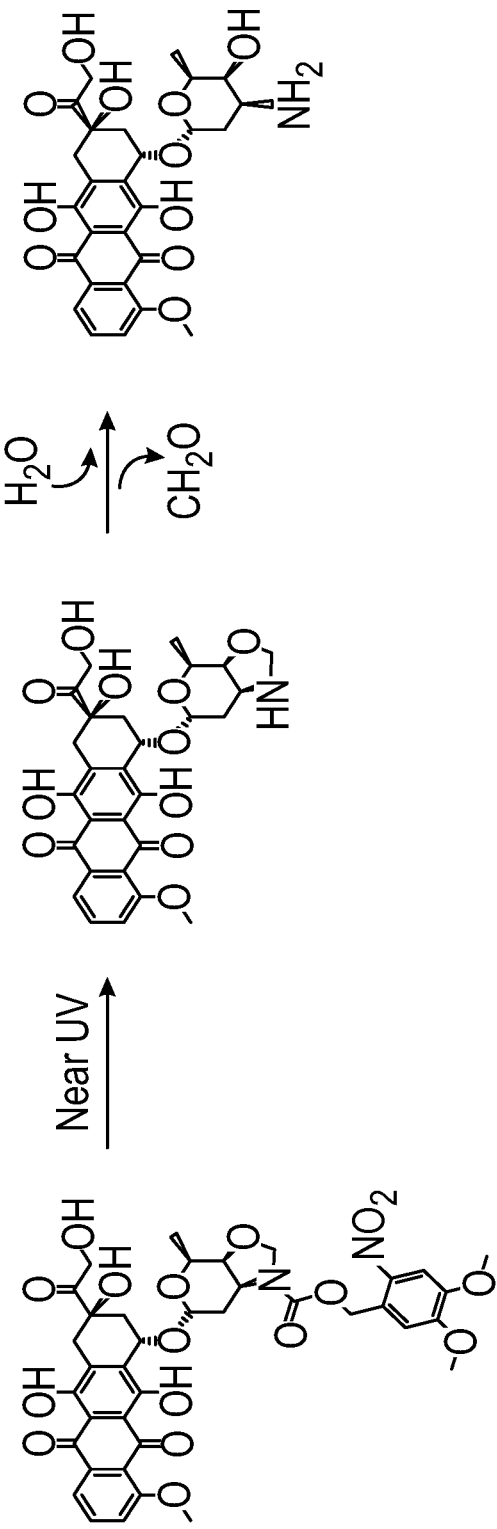
FIG. 1A is a chemical scheme depicting the activation of photodoxazolidine R=H by near UV light.

The present disclosure provides photo-activated prodrugs of doxazolidine, pharmaceutically-acceptable salts thereof, pharmaceutical compositions containing these prodrugs, and methods of treating cancer or other proliferative diseases or disorders in a subject by the administration of a therapeutically-effective amount of one or more of the compounds or compositions of this disclosure to the subject.

Compounds of the Disclosure

One aspect of the disclosure provides photoactivated prodrugs of doxazolidine, or pharmaceutically-acceptable salts thereof.

One compound of this disclosure is the photoactivated anticancer prodrug photodoxazolidine and pharmaceutically acceptable salts thereof and stereoisomers thereof:

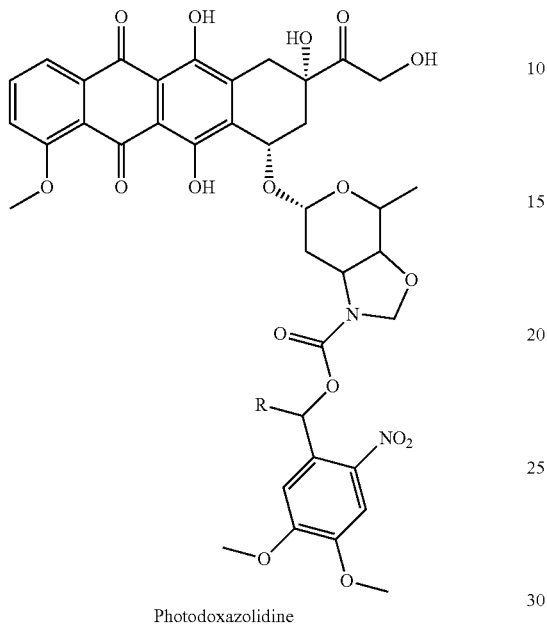

Photodoxazolidine wherein R is H or CH₃.

Another compound of this disclosure is the photoactivated anticancer prodrug Azido-PEG-Photodoxazolidine and pharmaceutically acceptable salts thereof and stereoisomers thereof:

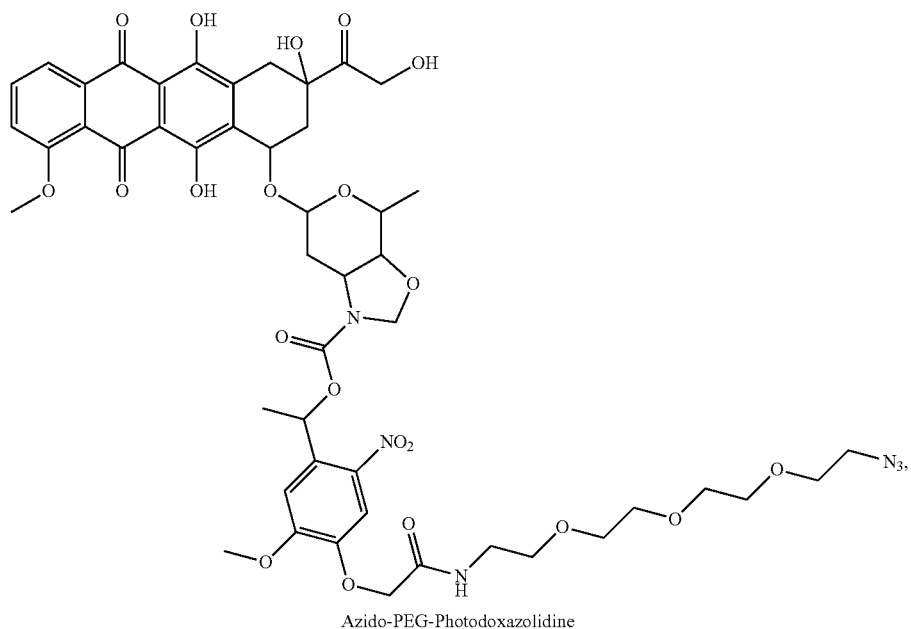 [SMILES: COc1cc(C(C)OC(=O)N2COC3C(C)OC(OC4CC(O)(C(=O)CO)Cc5c(O)c6c(c(O)c54)C(=O)c4c(OC)cccc4C6=O)CC32)c([N+](=O)[O-])cc1OCC(=O)NCCOCCOCCOCCN=[N+]=[N-]]

Azido-PEG-Photodoxazolidine

Another compound of this disclosure is the photoactivated anticancer prodrug MARCKS-PEG-Photodoxazolidine and pharmaceutically acceptable salts thereof and stereoisomers and regioisomers thereof:

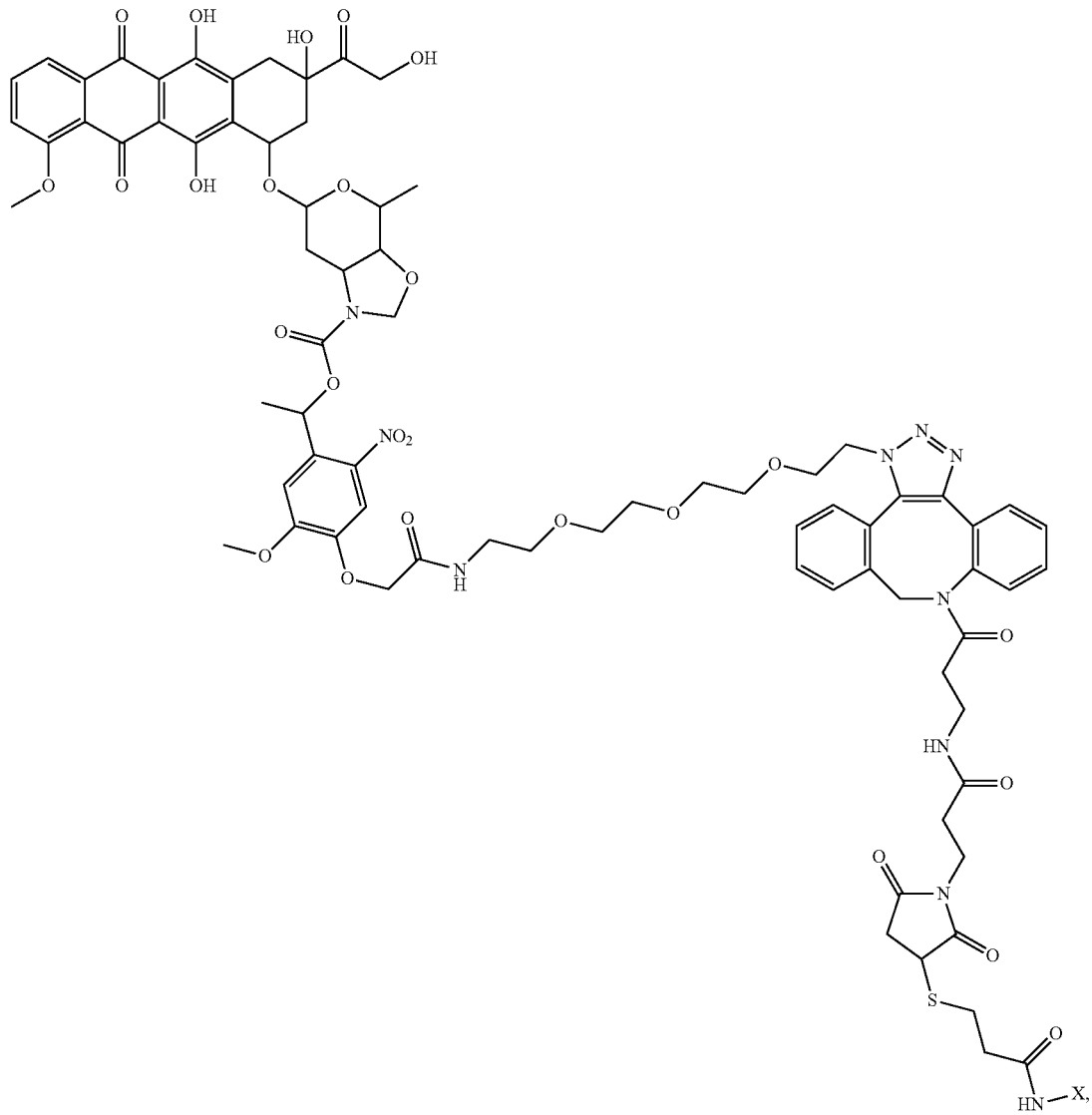

MARCKS-PEG-Photodoxazolidine wherein X is selected from: KKKKKRFSFKKSFKLSGFSFKKNKK (SEQ ID NO: 1), KKKKKRFSFKK (SEQ ID NO: 2), SFKLSGFSFKKNKK (SEQ ID NO: 3), RRRRRRRRRR (SEQ ID NO: 4), KKKKKKKKKK (SEQ ID NO: 5).

Another compound of this disclosure is the photoactivated anticancer prodrug Glucose-PEG-Photodoxazolidine and pharmaceutically acceptable salts thereof and stereoisomers thereof:

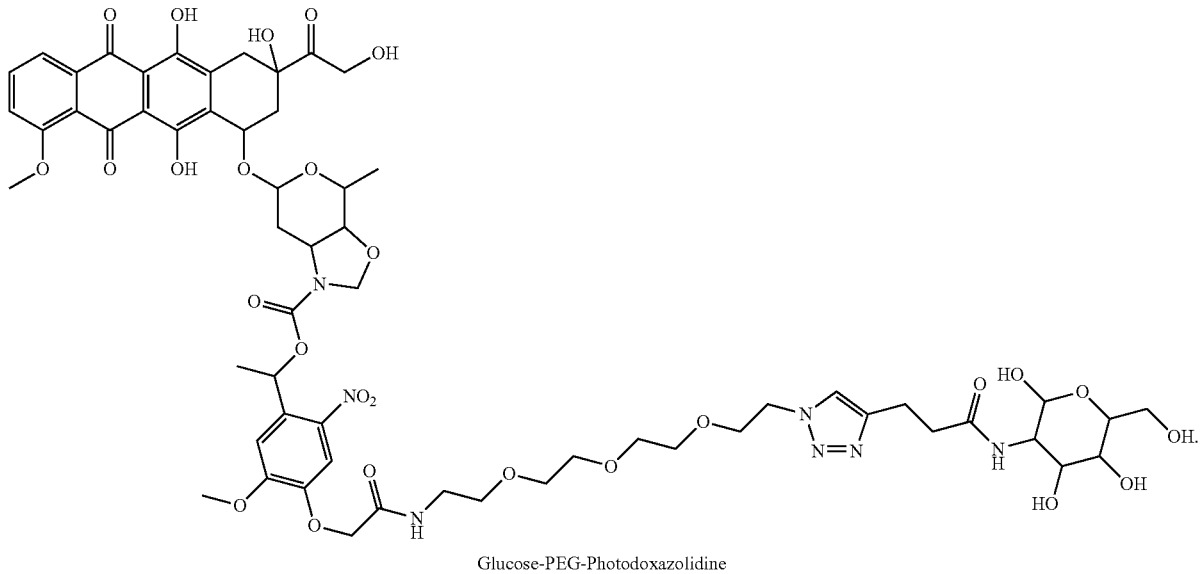 [SMILES: COc1cc(C(C)OC(=O)N2COC3C(C)OC(OC4CC(O)(C(=O)CO)Cc5c(O)c6c(c(O)c54)C(=O)c4c(OC)cccc4C6=O)CC32)c([N+](=O)[O-])cc1OCC(=O)NCCOCCOCCOCCn1cc(CCC(=O)NC2C(O)OC(CO)C(O)C2O)nn1]

Glucose-PEG-Photodoxazolidine

Another compound of this disclosure is the photoactivated anticancer prodrug Glucose-Photodoxazolidine and pharmaceutically acceptable salts thereof and stereoisomers thereof:

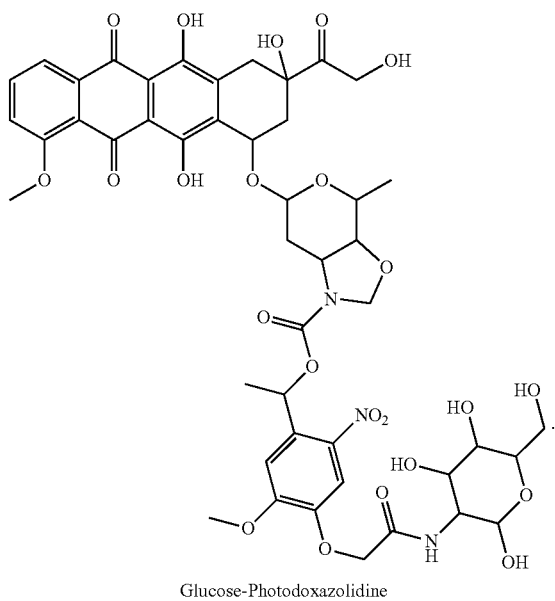 [SMILES: COc1cc(C(C)OC(=O)N2COC3C(C)OC(OC4CC(O)(C(=O)CO)Cc5c(O)c6c(c(O)c54)C(=O)c4c(OC)cccc4C6=O)CC32)c([N+](=O)[O-])cc1OCC(=O)NC1C(O)OC(CO)C(O)C1O]

Glucose-Photodoxazolidine

As used herein, the term "prodrug" refers to any compound that, when administered in a biological system, generates the drug substance, i.e. active ingredient, as a result of spontaneous chemical reaction(s), enzyme catalyzed chemical reaction(s), photolysis, and/or metabolic chemical reaction(s). A prodrug is thus a covalently modified analog or latent form of one or more therapeutically-active compound(s). The prodrugs of this disclosure may be activated by radiation, including UV light. This photo-activation may include co-administration of the compound(s) with 18-F-deoxyglucose (18-FDG) and/or exposure to radiation, such as UV light and/or Cherenkov radiation, which may result from PET scan.

Where the compounds according to this disclosure have at least one chiral center, they may accordingly exist as enantiomers. Where the compounds possess two or more chiral centers, they may additionally exist as diastereomers. Where the processes for the preparation of the compounds according to the disclosure give rise to mixtures of stereoisomers and/or regioisomers, these isomers may be separated by conventional techniques such as preparative chromatography. The compounds may be prepared in racemic form or as individual enantiomers or diastereomers by either stereospecific synthesis or by resolution. The compounds may, for example, be resolved into their component enantiomers or diastereomers by standard techniques, such as the formation of diastereoisomeric pairs by salt formation with an optically active acid, such as (−)-di-p-toluoyl-D-tartaric acid and/or (+)-di-p-toluoyl-L-tartaric acid followed by fractional crystallization and regeneration of the free base. The compounds may also be resolved by formation of diastereoisomeric esters or amides, followed by chromatographic separation and removal of the chiral auxiliary. Alternatively, the compounds may be resolved using a chiral HPLC column. It is to be understood that all stereoisomers, racemic mixtures, diastereomers and enantiomers thereof are encompassed within the scope of the present disclosure, and chemical structures that do not illustrate specific stereoisomers and/or regioisomers are intended to encompass all stereoisomers of that compound.

Any reference to compounds of this disclosure also includes a reference to a pharmaceutically acceptable salt thereof. For use in medicine, the salts of the anti-cancer compounds of this disclosure refer to non-toxic "pharmaceutically acceptable salts" (Ref. International J. Pharm., 1986, 33, 201-217; J. Pharm. Sci., 1997 (January), 66(1): 1). Other salts may, however, be useful in the preparation of compounds according to this disclosure or of their pharmaceutically acceptable salts.

"Pharmaceutically acceptable salts" include salts that retain the biological effectiveness of the free acids and bases of the specified compound and that are not biologically or otherwise undesirable. A compound of the disclosure may possess a sufficiently acidic, a sufficiently basic, or both functional groups, and accordingly react with any of a number of inorganic or organic bases, and inorganic and organic acids, to form a pharmaceutically acceptable salt. Examples of pharmaceutically acceptable salts include those salts prepared by reaction of the compounds of this disclosure with a mineral or organic acid or an inorganic base, such salts including sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyn-1,4-dioates, hexyne-1,6-dioates, benzoates, chlorobenzoates, methylbenzoates, dinitromenzoates, hydroxybenzoates, methoxybenzoates, phthalates, sulfonates, xylenesulfonates, pheylacetates, phenylpropionates, phenylbutyrates, citrates, lactates, γ-hydroxybutyrates, glycollates, tartrates, methanesulfonates, propanesulfonates, naphthalene-1-sulfonates, naphthalene-2-sulfonates, and mandelates. Because a single compound of this disclosure may include more than one acidic or basic moiety, the compounds of this disclosure may include mono-, di- or tri-salts in a single compound.

In the embodiments of the present disclosure in which the anti-cancer compound is a base, the desired pharmaceutically acceptable salt may be prepared by any suitable method available in the art, for example, treatment of the free base with an acidic compound, particularly an inorganic acid, such as hydrochloric acid, hydrobromic acid, sulfuric acid, nitric acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alphahydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

In the embodiments of the present disclosure in which the anti-cancer compound is an acid, the desired pharmaceutically acceptable salt may be prepared by any suitable method, for example, treatment of the free acid with an inorganic or organic base. Preferred inorganic salts are those formed with alkali and alkaline earth metals such as lithium, sodium, potassium, barium and calcium. Preferred organic base salts include, for example, ammonium, dibenzylammonium, benzylammonium, 2-hydroxyethylammonium, bis(2-hydroxyethyl)ammonium, phenylethylbenzylamine, dibenzylethylenediamine, and the like. Other salts of acidic moieties may include, for example, those salts formed with procaine, quinine and N-methylglusoamine, plus salts formed with basic amino acids such as glycine, ornithine, histidine, phenylglycine, lysine and arginine.

Additionally, some of the crystalline forms for the compounds may exist as polymorphs and as such are included in the present disclosure. In addition, some of the compounds may form solvates with water (i.e., hydrates) or common organic solvents, and such solvates are also intended to be encompassed within the scope of this disclosure.

Compositions of the Disclosure

When employed as pharmaceuticals, the compounds of this disclosure are administered in the form of pharmaceutical compositions. These compounds can be administered by a variety of routes including oral, rectal, transdermal, subcutaneous, intravenous, intramuscular, and intranasal. Preferably, the compounds of this disclosure are administered parenterally when used to treat a cancer, such as breast or ovarian cancer. Such pharmaceutical compositions are prepared in a manner well known in the pharmaceutical art and comprise at least one active anti-cancer compound of this disclosure.

The pharmaceutical compositions of this disclosure contain, as the active ingredient, one or more of the compounds of this disclosure, associated with pharmaceutically acceptable formulations. In making the compositions of this disclosure, the active ingredient is usually mixed with an excipient, diluted by an excipient or enclosed within a carrier which can be in the form of a capsule, sachet, paper or other container. An excipient is usually an inert substance that forms a vehicle for a drug. When the excipient serves as a diluent, it can be a solid, semi-solid, or liquid material, which acts as a vehicle, carrier or medium for the active ingredient. Thus, the compositions can be in the form of solutions, syrups, aerosols (as a solid or in a liquid medium), ointments containing, for example, up to 30% by weight of the active compound, soft and hard gelatin capsules, suppositories, sterile injectable solutions, and sterile packaged powders.

In preparing a formulation, it may be necessary to mill active compounds of the disclosure to provide the appropriate particle size prior to combining with the other ingredients. If the anti-cancer compound is substantially insoluble, it ordinarily is milled to a particle size of less than 200 mesh. If the compound(s) is substantially water soluble, the particle size is normally adjusted by milling to provide a substantially uniform distribution in the formulation, e.g. about 40 mesh.

Some examples of suitable excipients include lactose, dextrose, sucrose, sorbitol, mannitol, starches, gum acacia, gum Arabic, calcium phosphate, alginates, tragacanth, gelatin, calcium silicate, microcrystalline cellulose, polyvinylpyrrolidone, cellulose, sterile water, syrup, and methylcellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the disclosure can be formulated so as to provide quick, sustained or delayed release of the active ingredient after administration to the subject by employing procedures known in the art.

Pharmaceutical compositions of this disclosure suitable for parenteral administration comprise one or more compounds of the disclosure in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, solutes which render the formulation isotonic with the blood of the intended recipient or suspending or thickening agents.

Examples of suitable aqueous and nonaqueous carriers which may be employed in the pharmaceutical compositions of the disclosure include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as wetting agents, emulsifying agents, alkalinizing agents, antioxidants, chelating agents, coloring agents and dispersing agents. It may also be desirable to include isotonic agents, such as sugars, sodium chloride, and the like in the compositions. In addition, prolonged absorption of the injectable pharmaceutical form may be brought about by the inclusion of agents which delay absorption such as aluminum monosterate and gelatin.

For preparing solid compositions such as tablets, the principal active ingredient, including at least one compound of this disclosure, is mixed with a pharmaceutical excipient to form a solid preformulation composition containing a homogeneous mixture of a compound of this disclosure. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation is then subdivided into unit dosage forms of the type described above containing from, for example, 0.1 to about 500 mg of the active ingredient of the present disclosure.

Formulations of the disclosure suitable for oral administration may be in the form of capsules, cachets, pills, tablets, powders, granules or as a solution or a suspension in an aqueous or non-aqueous liquid, or an oil-in-water or water-in-oil liquid emulsions, or as an elixir or syrup, or as pastilles (using an inert base, such as gelatin and glycerin, or sucrose and acacia), and the like, each containing a predetermined amount of a compound or compounds of this disclosure as an active ingredient. A compound or compounds of this disclosure may also be administered as a bolus, electuary or paste.

In solid dosage forms of the disclosure for oral administration (capsules, tablets, pills, dragees, powders, granules and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monosterate; (8) absorbents, such as kaolin and bentonite clay; (9) lubricants, such as talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may be employed as fillers in soft and hard-filled gelatin capsules using such excipients as lactose or milk sugars, as well as high molecular weight polyethylene glycols and the like.

The tablets or pills of the present disclosure may be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release.

Formulations of the pharmaceutical compositions of the disclosure for rectal or vaginal administration may be presented as a suppository, which may be prepared by mixing one or more compounds of the disclosure with one or more suitable nonirritating excipients or carriers comprising, for example, cocoa butter, polyethylene glycol, a suppository wax or salicylate, and which is solid at room temperature, but liquid at body temperature and, therefore, will melt in the rectum or vaginal cavity and release the active compound. Formulations of the present disclosure which are suitable for vaginal administration also include pessaries, tampons, creams, gels, pastes, foams or spray formulations containing such carriers as are known in the art to be appropriate.

Dosage forms for the topical or transdermal administration of compounds of this disclosure include powders, sprays, ointments, pastes, creams, lotions, gels, solutions, patches, drops and inhalants. The active ingredient may be mixed under sterile conditions with a pharmaceutically-acceptable carrier, and with any buffers, or propellants which may be required. The ointments, pastes, creams and gels may contain, in addition to an active ingredient, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Pharmaceutical formulations include those suitable for administration by inhalation or insufflation or for nasal or intraocular administration. For administration to the upper (nasal) or lower respiratory tract by inhalation, the compounds of the disclosure are conveniently delivered from an insufflator, nebulizer or a pressurized pack or other convenient means of delivering an aerosol spray. Pressurized packs may comprise a suitable propellant such as dichlorodifluoromethane, trichlorofluoromethane, dichlorotetrafluoroethane, carbon dioxide, or other suitable gas. In the case of a pressurized aerosol, the dosage unit may be determined by providing a valve to deliver a metered amount.

Alternatively, for administration by inhalation or insufflation, the composition may take the form of a dry powder, for example, a powder mix of one or more compounds of the disclosure and a suitable powder base, such as lactose or starch. The powder composition may be presented in unit dosage form in, for example, capsules or cartridges, or, e.g., gelatin or blister packs from which the powder may be administered with the aid of an inhalator, insufflator or a metered-dose inhaler.

For intranasal administration, compounds of the disclosure may be administered by means of nose drops or a liquid spray, such as by means of a plastic bottle atomizer or metered-dose inhaler. Typical of atomizers are the Mistometer (Wintrop) and Medihaler (Riker).

Drops, such as eye drops or nose drops, may be formulated with an aqueous or nonaqueous base also comprising one or more dispersing agents, solubilizing agents or suspending agents. Liquid sprays are conveniently delivered from pressurized packs. Drops can be delivered by means of a simple eye dropper-capped bottle or by means of a plastic bottle adapted to deliver liquid contents dropwise by means of a specially shaped closure.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug is accomplished by dissolving or suspending the drug in an oil vehicle.

Injectable depot forms are made by forming microencapsule matrices of the drug in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly (anhydrides). Depot injectable formulations are also prepared by entrapping the drug in liposomes or microemulsions which are compatible with body tissue. The injectable materials can be sterilized for example, by filtration through a bacterial-retaining filter.

The formulations may be presented in unit-dose or multi-dose sealed containers, for example, ampules and vials, and may be stored in a lyophilized condition requiring only the addition of the sterile liquid carrier, for example water for injection, immediately prior to use. Extemporaneous injection solutions and suspensions may be prepared from sterile powders, granules and tablets of the type described above.

A preferred formulation of this disclosure is a monophasic pharmaceutical composition suitable for parenteral or oral administration for the treatment or prophylaxis of a cancer, consisting essentially of a therapeutically-effective amount of at least one compound of the disclosure, and a pharmaceutically acceptable carrier.

Methods of Making Compounds of the Disclosure

During any of the processes for preparation of the compounds of this disclosure, it may be necessary and/or desirable to protect sensitive or reactive groups on any of the molecules concerned. This may be achieved by means of conventional protecting groups, such as those described in Protective Groups in Organic Chemistry, ed. J. F. W. McOmie, Plenum Press, 1973; and T. W. Greene & P. G. M. Wuts, Protective Groups in Organic Synthesis, John Wiley & Sons, 1991. The protecting groups may be removed at a convenient subsequent stage using methods known in the art.

"Protecting group" refers to a moiety of a compound that masks or alters the properties of a functional group or the properties of the compound as a whole. The chemical substructure of a protecting group varies widely. One function of a protecting group is to serve as intermediates in the synthesis of the parental prodrug substance. Chemical protecting groups and strategies for protection/deprotection are well known in the art. See: "Protective Groups in Organic Chemistry", Theodora W. Greene (John Wiley & Sons, Inc., New York, 1991, which is incorporated herein by reference. Protecting groups are often utilized to mask the reactivity of certain functional groups, to assist in the efficiency of desired chemical reactions, e.g. making and breaking chemical bonds in an ordered and planned fashion. Protection of functional groups of a compound alters other physical properties besides the reactivity of the protected functional group, such as the polarity, lipophilicity (hydrophobicity), and other properties which can be measured by common analytical tools. Chemically protected intermediates may themselves be biologically active or inactive.

Intermediates and compounds provided by this disclosure may be prepared by the reaction sequence depicted in Examples 1, and 3-6, of this disclosure. Thus, this disclosure provides methods of synthesizing the prodrug compounds of this disclosure as described in these Examples.

Methods of Using Compounds of the Disclosure

In the methods of using the compounds of this disclosure, the term "subject" refers to mammals such as humans or primates, such as apes, monkeys, orangutans, baboons, gibbons, and chimpanzees. The term "subject" can also refer to companion animals, e.g., dogs and cats; zoo animals; equids, e.g., horses; food animals, e.g., cows, pigs, and sheep; and disease model animals, e.g., rabbits, mice, and rats. The subject can be a human or non-human. The subject can be of any age. For example, in some embodiments, the subject is a human infant, i.e., post natal to about 1 year old; a human child, i.e., a human between about 1 year old and 12 years old; a pubertal human, i.e., a human between about 12 years old and 18 years old; or an adult human, i.e., a human older than about 18 years old. In some embodiments, the subject is an adult, either male or female. In this disclosure, reference to a "patient," an "individual," or a "mammal" is/are used interchangeably for the term "subject."

As used herein, the terms "treat" and "treatment" refer to both therapeutic treatment and prophylactic or preventative measures, wherein the object is to prevent or slow down (lessen) an undesired physiological condition or disease, or obtain beneficial or desired clinical results. The term "treatment" also refers to the alleviation of symptoms associated with the above conditions or diseases.

Thus, this disclosure provides methods of treating cancer in a subject comprising administering an effective amount of at least one compound of this disclosure to a subject in need thereof. The therapeutically-active compounds of this disclosure are effective over a wide dosage range and are generally administered in a therapeutically-effective amount. The dosage and manner of administration will be defined by the application of the anti-cancer agent and can be determined by routine methods of clinical testing to find the optimum dose. It will be understood, however, that the amount of the compound actually administered will be determined by a physician, in the light of the relevant circumstances, including the condition to be treated, the chosen route of administration, the actual compound administered, the age, weight, and response of the individual subject, the severity of the subject's symptoms, and the like.

The administration of the prodrug compounds of the disclosure may include both local and/or systemic administration. Local administration results in significantly more delivery of a composition to a specific location as compared to the entire body of the subject, whereas, systemic administration results in delivery of a composition to essentially the entire body of the subject.

Whereas most of the results of in vivo anti-cancer activity of compounds of this disclosure are obtained by parenteral administration of the compounds, the reference compound doxorubicin is known to be active after oral administration.

Routes of administration suitable for a method of treating brain cancer include both central and peripheral administration. Central administration results in delivery of a composition to essentially the central nervous system of the subject and includes, e.g., intrathecal administration, or epidural administration, as well as a cranial injection or implant. Peripheral administration results in delivery of a composition to essentially any area of a subject outside of the central nervous system and encompasses any route of administration other than direct administration to the spine or brain.

This disclosure further provides a method of treating cancer in the subject, which includes administering an effective amount of a pharmaceutical composition of this disclosure to a subject in need thereof. Such compositions generally comprise a therapeutically effective amount of at least one compound of the disclosure, that is, an amount effective to ameliorate, lessen, inhibit or destroy neoplastic tissue. Such amounts typically comprise from about 0.1 to about 1000 mg of the compound per kilogram of body weight of the subject to which the composition is administered. Therapeutically effective amounts can be administered according to any dosing regimen satisfactory to those of ordinary skill in the art.

A related embodiment of the disclosure provides the use of any of the compounds or compositions of this disclosure in the preparation of a medicament for the treatment of cancer.

Another embodiment of the disclosure relates to any of the compounds or compositions of this disclosure for use in the treatment of a cancer.

Administration is typically by various parenteral means. Pharmaceutical compositions of this disclosure, suitable for parenteral administration, generally include various aqueous media.

Alternatively, compositions can be administered orally in solid dosage forms, such as capsules, tablets and powders; or in liquid forms such as elixirs, syrups, and/or suspensions.

Each publication or patent cited herein is incorporated herein by reference, in its entirety. Aspects of this invention, having been generally described will be more readily understood by reference to the following examples, which are included merely for the purposes of illustration of aspects of the embodiments of the present disclosure. The examples are not intended to limit the disclosure, as one of skill in the art would recognize from the above teachings and the following examples that other techniques and methods can satisfy the claims and can be employed without departing from the scope of the claimed disclosure.

EXAMPLES

Example 1: Synthesis of Photodoxazolidines

Summary: Photodoxazolidine (without a methyl at the benzylic position, R=H) is easily synthesized in two steps from 4,5-dimethoxy-2-nitrobenzyl alcohol and doxazolidine: commercial 4,5-dimethoxyl-2-nitrobenzyl alcohol is first reacted with p-nitrophenylchloroformate to give the p-nitrophenyl carbonate of the benzyl alcohol derivative. The p-nitrophenyl carbonate is then reacted with doxazolidine to give photodoxazolidine. A synthesis scheme for photodoxazolidine with the methyl at the benzylic position R=Me is depicted in FIG. 1B. These structures of photodoxazolidine can be completely characterized by high resolution one- and two-dimensional NMR spectroscopy.

Reagents and Instrumentation: Doxazolidine/Doxoform was synthesized from doxorubicin free base derived from lactose-containing clinical preparations of doxorubicin hydrochloride as previously described (Barthel, et al., J Med Chem 2012, 55: 6595-607). NMR spectra were acquired on a Varian Unity Inova spectrophotometer (Palo Alto, Calif.) at 500 MHz in deuterated solvents from Cambridge Isotope Laboratories, Inc. (Andover, Mass.). The spectra were analyzed with MestReNova software, version 10 (Mestrelab Research S. L., Santiago de Compostela, Spain). Chemical shift values are reported in parts per million (ppm) on the $\delta$ scale and standardized to the residual solvent peak. Concentrations of all anthracycline-containing compounds were measured by absorbance at 480 nm on a Hewlett-Packard/Agilent 8452A diode-array instrument, using a constant extinction coefficient of 11,500 $M^{-1}$ $cm^{-1}$ in 75% DMSO/25% water. Analytical HPLC was performed on an Agilent 1050/1100 hybrid instrument equipped with a 1050 series autoinjector, a 1100 series UV/visible diode-array detector, and a 1046A fluorescence detector. An Agilent Zorbax octadecylsilyl (C18) reverse-phase column (4.6 mm i.d.× 150 mm, 5 μm) was used and the mobile phases were mixtures of acetonitrile (ACN) and acidic phosphate buffer (15 mM $KH_2PO_4$, pH 4.6). Elution Method 1 used timetable and mobile-phase conditions as follows: 0 min (30% ACN, 1 mL/min), 3 min (30% ACN, 1 mL/min), 5.5 min (70% ACN, 1 mL/min), 6-9 min (80% ACN, 1.5 mL/min), 10 min (30% ACN, 1.5 mL/min), 11.5 min (30% ACN, 1 mL/min). Method 2 used conditions of: 0-2 min (25% ACN, 1 mL/min), 6 min (60% ACN, 1 mL/min), 8.5-11.5 min (80% ACN, 2 mL/min), 12.5 min (25% ACN, 1.5 mL/min), 13.5 min (25% ACN, 1 mL/min). Compounds were detected by absorbance at wavelengths of 350 and 480 nm. All chemicals were purchased from Aldrich (Milwaukee, Wis.) or Fisher Scientific, Inc. (Fair Lawn, N.J.) unless otherwise noted.

Synthesis of 4,5-Dimethoxy-2-nitrobenzyl-p-nitrophenyl carbonate (DMNA-pNP): 4,5-Dimethoxy-2-nitrobenzyl alcohol (2.1 g, 9.7 mmol) was added to an oven-dried round bottom flask and dissolved in 100 mL of anhydrous THF. To this, p-nitrophenyl chloroformate (2.6 g, 1.3 equiv) was added, followed immediately by diisopropylethylamine (1.5 equiv) and a catalytic amount of dimethylaminopyridine (0.1 equiv). The reaction was allowed to proceed at room temperature in the dark and under a nitrogen atmosphere. After reacting overnight, an off-white precipitate had formed. A small amount of the reaction mixture was centrifuged to separate the precipitate from the yellow supernatant. HPLC (method 1) and TLC (elution with 50:1 chloroform:methanol) of both fractions indicated that the precipitate was about 90% pure product, with the only contaminant being p-nitrophenol. The supernatant was a mixture of product, all starting materials, and p-nitrophenol. The reaction was allowed to continue a second night, after which the precipitate was collected by filtration through a glass-fritted funnel. The filtrate was collected and additional product precipitated by the addition of ice-cold, slightly-basic phosphate buffer (50 mM $Na_2HPO_4$, pH 8.0). This precipitate was collected by centrifugation (10,000×g, 4° C.), redissolved in THF, and precipitated a second time, after which it was approximately 85% product and 15% p-nitrophenol by NMR. Additional purification was not undertaken for this material, as purification by silica gel radial chromatography would have resulted in large amounts of irradiation of the nearly colorless, photosensitive product by high-intensity UV light used to monitor the chromatography. Additionally, p-nitrophenol is a product of the coupling of doxazolidine to DMNA-pNP; a small amount of contaminating p-nitrophenol forward was unlikely to be a hindrance to the progress of the coupling reaction. Structural characterization of the 85%-pure material was performed by proton NMR, with assignments assisted by homonuclear COSY: $^1$H NMR (500 MHz, chloroform-d) $\delta$ 4.00 (s, 3H, 5-OCH$_3$), 4.04 (s, 3H, 4-OCH$_3$), 5.73 (s, 2H, Bn), 7.12 (s, 1H, 6), 7.41-7.46 (m, 2H, 2' and 6'), 7.79 (s, 1H, 3), 8.28-8.33 ppm (m, 2H, 3' and 5'). Residual p-nitrophenol signals were visible at $\delta$ 7.50-7.53 (m, 2 and 6), 8.34-8.38 ppm (m, 3 and 5).

Synthesis of Photodoxazolidine R=H: For the synthesis of photodoxazolidine R=H, 220 mg (0.40 mmol) of a mixture of doxazolidine and doxoform (about 3:1 molar ratio) was dissolved in DMSO (dried over 4A molecular sieves) and placed into an oven-dried round-bottom flask equipped with a stir bar. DMNA-pNP (6 equiv) and HOBt (1.5 equiv) were added to the DMSO and the reaction proceeded with stirring under a nitrogen atmosphere at room temperature in the dark. The first progress measurement, analyzed by HPLC 2 h (method 2) after beginning of the reaction, showed that all the doxazolidine/doxoform had been consumed. To simplify purification, any remaining doxazolidine/doxoform was hydrolyzed to doxorubicin by slight acidification of the reaction with the addition of 10% HCl in water to a final HCl concentration of 0.2% and stirring at room temperature for 30 min. The water-insoluble photodoxazolidine was then precipitated with the addition of 5 volumes of cold acidic phosphate buffer (20 mM $NaH_2PO_4$, pH 6.0), collected by centrifugation (10,000×g, 4° C.), and the precipitate washed with cold HPLC grade water. The wet, red solid was dissolved in chloroform, transferred to a separatory funnel, and washed with brine, thereby collecting a moderately dry chloroform solution. Initial purification of the product was accomplished by radial chromatography without UV light by observing the progress of the major red band and eluting with 30:1 chloroform:methanol. This method served to purify away minor anthracycline contaminants, but HPLC and TLC analysis of the collected fractions indicated continued contamination by p-nitrophenol. Therefore, final purification was done by dissolving the combined best fractions in DMSO and precipitating photodoxazolidine away from p-nitrophenol with 4-5 volumes of cold basic phosphate buffer (50 mM $Na_2HPO_4$, pH 8.5). The precipitate was collected by centrifugation (10,000× g at 4° C.), the supernatant removed, and the pellet redissolved in DMSO for continued precipitation until the supernatant was no longer yellow, which occurred after the 5th round of precipitation. The pellet was then washed by dispersing it into cold HPLC grade water, and the solid was collected by vacuum filtration through a glass-fritted funnel and air-dried overnight in the dark. Finally, the red material was dissolved from the frit with chloroform, collected into a round-bottom flask, and the solvent first removed by rotary evaporation then under high vacuum. Final purity was >95% as measured by HPLC, TLC, and high-temp (50° C.) $^1$H-NMR and the final yield was 62%. Structural characterization was assisted by homonuclear COSY, HMBC, and HSQC at 50° C.: 1H NMR (500 MHz, Chloroform-d, see Chart 1 for numbering scheme) δ 1.39 (d, J=7 Hz, 3H, 5'-CH3), 1.47 (s, 1H, 2'), 1.85 (m, 1H, 2'), 2.17 (dd, J=4.0, 15 Hz, 1H, 8), 2.46 (d, J=15 Hz, 1H, 8), 2.94 (t, J=5 Hz, 1H, 14-OH), 3.06 (d, J=19 Hz, 1H, 10), 3.29 (dd, J=2.0, 19 Hz, 1H, 10), 3.93 (s, 6H, 4"-OCH3 and 5"-OCH3), 4.05 (dd, J=2, 7 Hz, 1H, 4'), 4.08 (s, 3H, 4-OCH3), 4.12-4.22 (m, 2H, 3' and 5'), 4.67 (s, 1H, 9-OH), 4.75 (d, J=5 Hz, 2H, 14), 5.01 (d, J=4 Hz, 1H, O—CH2-N), 5.06 (d, J=4 Hz, 1H, O—CH-2-N), 5.31-5.36 (m, 1H, 7), 5.49 (t, J=5 Hz, 1H, 1'), 5.55 (s, 2H, Bn), 6.98 (s, 1H, 6"), 7.39 (d, J=8 Hz, 1H, 3), 7.69 (s, 1H, 3"), 7.77 (d, J=8 Hz, 1H, 2), 8.05 (d, J=8 Hz, 1H, 1), 13.21 (s, 1H, phenolic), 13.92 (s, 1H, phenolic).

Example 2: In Vitro and In Vivo Characterization of Photodoxazolidine

Quantum Yield:

Initially, measurement of the quantum yield of photodoxazolidine R=H was done in a fully-absorbing solution of photoactive drug in a solution of 90% dimethylacetamide (DMA), 10% water in a 1×1 cm quartz cuvette equipped with a small magnetic stir bar. A stock of photodoxazolidine in DMA was diluted in 9:1 DMA:$H_2O$ to a final concentration of 373 µM in a final volume of 3.380 mL. Spectroscopy measurements indicated that the absorbance of this solution at 325 nm was greater than 2.5. The cuvette was placed into the path of an Omnichrome He-Cd laser (single-window power: 10.75 mW at 325 nm using a Scientech laser power meter). The solution was mixed by the stir bar, which was agitated with a magnetic stir plate placed vertically next to the cuvette. Aliquots of 20 µL were removed at times between 0 and 62 min of irradiation and those aliquots were analyzed by HPLC (method 2) for the ratio of dox to photodoxazolidine. The quantum yield was calculated from the ratio of molecules of doxorubicin (dox) formed to photons absorbed.

Figure 1B:
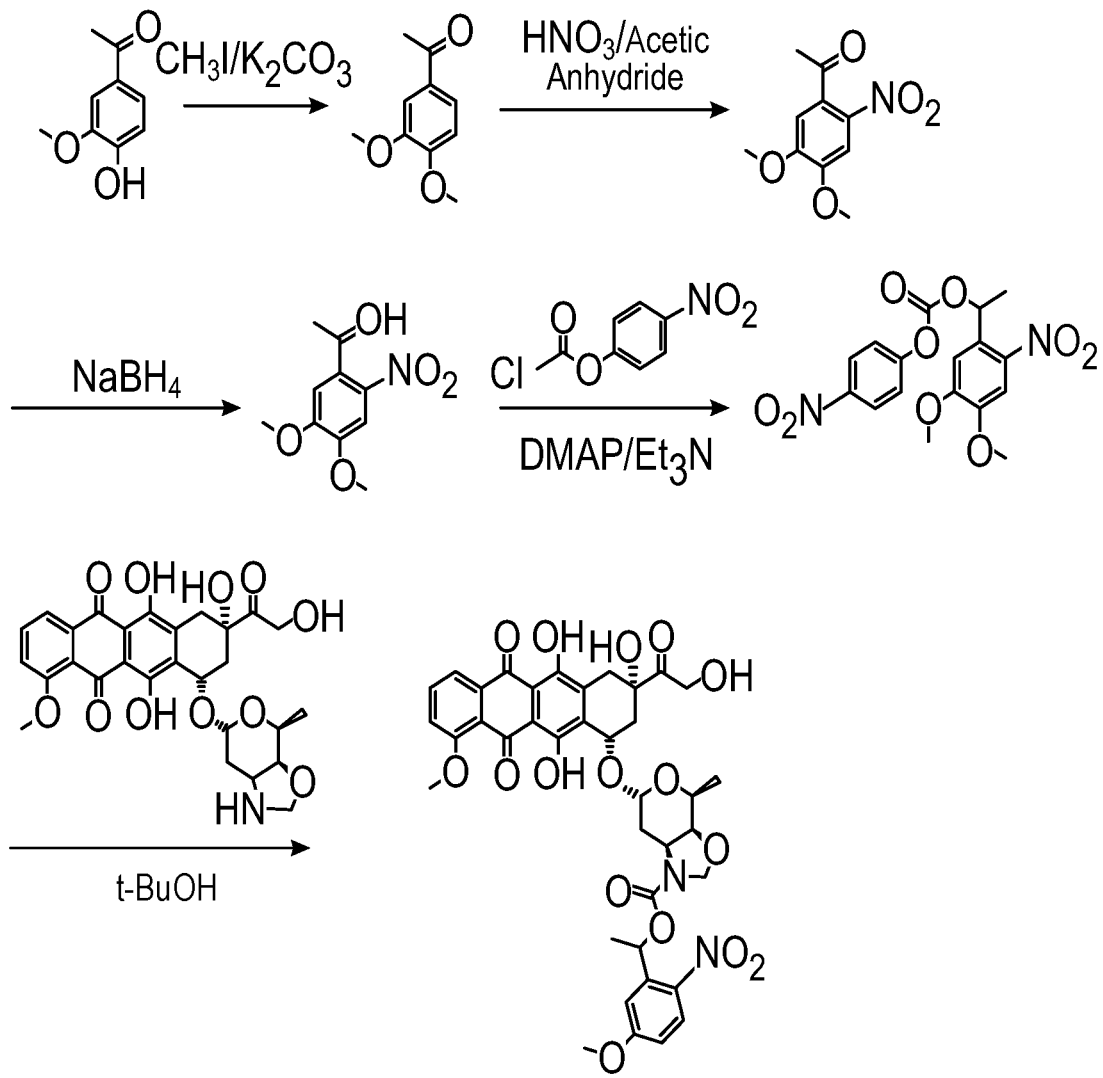
FIG. 1B shows a chemical synthesis scheme for photodoxazolidine R=Me.

Photoactivation of photodoxazolidine with near UV light gave doxorubicin with doxazolidine as a transient intermediate, as shown in the scheme depicted in FIG. 1A. Using the methodology described above, the quantum yield was 0.002.

To allow for better comparison between the quantum yield of photocleavage of photodoxazolidine with the quantum yield for azido-PEG-photodoxazolidine, the measurement was retaken with 50% acetonitrile in water as a solvent. Poor solubility in this solvent system necessitated the use of a 10 cm path quartz cell. Photodoxazolidine (in DMF) was diluted with 30 mL of 50% acetonitrile to a final concentration of 104 µM. The solution was confirmed to be fully absorbing by monitoring the laser power exiting the cell throughout the course of the experiment, which never deviated from 0 mW. As above, the contents of the cell were mixed with a small magnetic stir bar. Aliquots of 50 µL were removed at various times and analyzed as described above. The calculated quantum yield in this solvent system was identical to that measured from the DMF/$H_2O$ system used above.

Photolysis Timecourses:

In order to investigate the photolysis of the drugs in a system amenable to cell culture use, a custom UV irradiation apparatus was constructed, consisting of 3 small blacklight fluorescent bulbs (Southern New England Ultraviolet Co., $\lambda_{max}$=350 nm) set between two ring stands and suspended at a height of 11.5 cm. The bulbs' housing was reflective aluminum so as to direct as much UV irradiation as possible downward toward the plate. Upon installation in sterile cell culture hood, the power of the system was measured at approximately 6-7 mW using a Scientech laser power meter. Prior to experimentation, the hood and irradiation apparatus was sterilized with 254 nm germicidal UV irradiation overnight. Using this setup, 100 µM of 4,5-dimethoxy-2-nitrobenyl alcohol (DMNA), photodoxazolidine R=H, and glucose-PEG-photodoxazoldine were irradiated in individual wells of a 24-well plate. Initially, 50 µL of a DMSO stock was diluted with 950 µL of PBS and aliquots of 50 µL were removed at various times (0-180 min), mixing by pipetting each time. The timepoints were analyzed by HPLC (method 2) and plotted as fractional conversion versus time. However, it was noticed that this solvent system (5% DMSO/ 95% PBS) resulted in eventual precipitation of photodoxazolidine. Therefore, a second experiment was performed in which the PBS was replaced with 1:1 acetonitrile:water. With this system of 5% DMSO/47.5% acetonitrile/47.5% water, no visible precipitation was produced over the course of the reaction.

Cell Culture:

The ovarian carcinoma line NCl/ADR-RES (ADR) was grown in high-glucose Dulbecco's Modified Eagle Medium (DMEM) supplemented with 10% fetal bovine serum (FBS), 200 units/mL of penicillin and 200 μg/mL of streptomycin. The breast carcinoma line MDA-MB-231 was cultured in low-glucose DMEM with the same additives. Both lines were maintained in a humidified incubator with 5% $CO_2$/95% air at 37° C. UV irradiations were performed with the apparatus described above.

Tumor Cell Growth Inhibition:

Growth inhibition experiments were performed by seeding cells into 96-well plates or 24-well plates at densities of 1000-1500 cells per well or 8000 cells per well, respectively, and allowing the cells to adhere overnight. The media was then replaced with a range of aqueous concentrations of the drug in question and allowed to incubate at 37° C. with the cells for a span of time (Inc1) which ranged from 1 min to 48 hours. Irradiation was performed at room temperature with the plate's lid removed and ranged from 1 to 30 min. In some experiments, the drug solution was removed following Inc1 and irradiated in clean media or PBS. Following irradiation, the cells were placed back into the 37° C. incubator for a second period of incubation (Inc2), which varied between 1 min and 24 h, prior to replacement with fresh media. Plates which received no irradiation but identical treatment otherwise were done in parallel. The cells were then grown until the no-drug control wells reached approximately 80% confluence or 5 days, whichever was shorter. For experiments which contained both irradiated and nonirradiated plates, the entire experiment was worked up when 80% confluence was reached for any plate. The cells were fixed with 5% formalin in PBS, stained with crystal violet, washed with tap water, and air-dried. The stain was resolubilized in 50% isopropyl alcohol, 50% $H_2O$ containing 2% (w/v) SDS. The staining density was read on a multiwell plate reader at 588-600 nm. Percentage cell density was calculated relative to the irradiated no-drug control wells, plotted as a function of drug concentration, and fit using non-linear least squared analysis with a variable-slope dose response model in GraphPad Prism 5.0 software.

In early experiments, irradiation time was shown to have a significant cytotoxic effect on the growth of both ADR and 231 cells for irradiations longer than 15-20 min. Although the introduction of a long-pass glass filter between the light source and the plate alleviated this effect to a small extent, a maximum irradiation time of 10 min was settled upon. Additionally, we observed that, for ADR cells in particular, the use of PBS for Inc1, the irradiation, and Inc2 resulted in suspension of the culture. Since a media change at that point would remove the cells as well, the re-adherence of the cell population was accomplished by the addition of a large volume (200 μL) of complete media following Inc2, and overnight incubation. Then, a full media change was done to remove the drug. To avoid this, the cells were thereafter treated with drug dissolved in 1:1 PBS:serum-free DMEM, which did not result in loss of culture adherence. In later experiments examining the effects of glucose concentration, drug solutions were made with or without 50 mM glucose. Finally, additional experiments indicated that the length of Inc2 was generally irrelevant to the end result; if Inc1 and the irradiation time were equivalent, short (1-5 min) and long (24 h) times for Inc2 resulted in very little difference in the final IC50. Therefore, Inc2 was eventually standardized to the window between 30 min and 1 h.

Tumor Cell Uptake:

Uptake of the drugs by the cells was measured by flow cytometry. The cells were incubated with 500 nM photodoxazolidine R=H, azido-PEG-photodoxazolidine, or doxorubicin dissolved in 1:1 PBS:serum-free media for between 30 min and 4 h, after which the drug was removed and the cells washed with cold PBS. Cells were trypsinized to a single-cell suspension, rinsed again in cold PBS, and stored on ice for analysis by flow cytometry, monitoring the presence of the anthraquinone fluorophore (channel FL2). Cell populations were gated for intact cells in the side-scatter/forward-scatter plot and 10,000 gated events were scored for each timepoint. The mean fluorescence of the population was compared to the mean fluorescence of 10,000 gated events for an untreated population and the fold increase over background was plotted versus time of drug incubation.

In Vivo Formulation:

For reconstitution for intravenous injection into mice, dry photodoxazolidine R=H (23 mg) was dissolved in 785 μL of DMSO for a final concentration of 34.5 mM, labeled "Drug Stock," and stored dark at −20° C. Shortly before injection, the Drug Stock was thawed and 20-50 μL was transferred to a new tube. To this tube, 6 volumes (relative to the Drug Stock volume) of PEG-400 and 4 volumes of propylene glycol (PG) were added and the solution thoroughly mixed by vortexing. Immediately prior to injection, 9 volumes of saline (0.9% NaCl) was added to the DMSO/PEG/PG solution of photodoxazolidine and mixed by vortexing. The formulation was moderately turbid but failed to aggregate further. Pilot experiments demonstrated that upon a simulated injection in which 100 μL of the formulated material was diluted into 1.8 mL of saline (approximating the dilution of a 100 μL injection into a 25 g mouse) all turbidity disappeared and the drug was fully in solution. Therefore, this formulation was used as prepared. This protocol produces a final formulation of 5% DMSO, 30% PEG-400, 20% PG, 45% saline. A standard injection of 100 μL of this formulation delivers 4 mg dox equivalent/kg body weight for a mouse weighing 0.025 kg.

In Vivo Mouse Efficacy Experiment:

Luciferase-positive MDA-MB-231 cells were maintained in MEM culture medium supplemented with 10% heat inactivated fetal bovine serum and 2% penicillin/streptomycin. Prior to injection, typsinized cell populations were counted with a Z1 Coulter Particle counter, centrifuged, and resuspended in Hank's Balanced Salt Solution (HBSS) at a concentration of $4.0 \times 10^7$ cells/mL. Female nude mice (13) were each injected in the right mammary fat pad with two million cells (50 μL) from this suspension. Tumors were allowed to grow for two weeks prior to treatment. The 13 mice were divided into three groups: control 1 (4 mice) received 18-FDG (2-$^{18}$fluoro-2-deoxyglucose); control 2 (4 mice) received doxorubicin in saline at 4 mg/kg; treatment (5 mice) received 18-FDG+ photodoxazolidine R=H at 4 mg/kg dox equivalent weight, formulated as described above. 18-FDG (350-500 μCi) was given ip 40 min before vehicle or drug, which were each given iv. Treatment continued weekly for a total of six treatments. Body weight and tumor growth were measured regularly. Tumor growth was measured optically from the bioluminescence signal from injection of luciferin.

Cytotoxic Activity of all Photodoxazolidine Prodrugs was Significantly Enhanced by UV Irradiation:

Early testing with photodoxazolidine was performed in the multi-drug resistant ovarian cancer cell line NCl/ADR-RES (ADR cells) and irradiations were performed using a custom-built apparatus (described above). Initially, the cells were irradiated with unfiltered UV for 30 min; however, this resulted in nearly 100% die-off of these cells and loss of the experiment. Therefore, a high-pass filter (window glass) was introduced between the cells and the light source to limit the exposure of the cells to shorter wavelength radiation. Additionally, irradiations were limited to 10 min. Additional modifications were made to the initial procedure, including irradiating the cells in a 1:1 mixture of PBS and serum-free media, due to the propensity of the cells to detach from the dish when PBS alone was used. With our finalized protocol, significant cytotoxicity of photodoxazolidine R=H was dependent upon UV irradiation (Table 1). When treated alone, photodoxazolidine produced an IC50 of approximately 3.5 µM, a value which is 2-3 times more toxic than doxorubicin alone. However, when the prodrug was activated by near UV irradiation (principal emission 350 nm) for 10 min, the IC50 of photodoxazolidine dropped more than 30-fold to 110 nM. MDA-MB-231 breast cancer cells (231 cells) behaved similarly, with prodrug alone giving an IC50 of about 1600 nM and dropping approximately 22-fold to 73 nM when the treatment was combined with 10 min of near UV irradiation.

In addition to photodoxazolidine R=H, the growth inhibitory activity of azido-PEG-photodoxazolidine and glucose-PEG-photodoxazolidine were also measured (Table 2). Interestingly, although the measured quantum yields for activation of photodoxaz and azido-PEG-photodoxaz are different by about 5-10-fold, the IC50 values are fairly similar for equal UV exposure time. Glucose-PEG-photodoxazolidine, which was very non-toxic as the prodrug alone, was significantly more cytotoxic than photodoxazolidine upon UV irradiation, perhaps due to active uptake by 231 cells.

TABLE 1

IC50 values (nM) for dox, doxaz, and photodoxazolidine R=H.

| Cell lines | Dox (3 h) | Doxaz (3 h) | Photodoxaz (Alone) | Photodoxaz (10 min UV) |
|---|---|---|---|---|
| NCI/ADR-RES | 10,000 ± 1300 | 3 ± 0.2 | 3500 ± 800 | 110 ± 20 |
| MDA-MB-231 | 360 ± 30 | 5 – 10 | 1600 ± 120 | 73 ± 13 |

TABLE 2

IC50 values (nM) for photodoxazolidine R=H, azido-PEG-photodoxazolidine, and glucose-PEG-photodoxazolidine.

| | Photodoxazolidine | | Azido-PEG-photodoxazolidine | | Glucose-PEG-photodoxazolidine | |
|---|---|---|---|---|---|---|
| Cell lines | Prodrug Alone | +UV (10 min) | Prodrug Alone | +UV (10 min) | Prodrug Alone | +UV (10 min) |
| NCI/ADR-RES | 3500 ± 800 | 110 ± 20 | — | 81 ± 7 | — | — |
| MDA-MB-231 | 1600 ± 120 | 73 ± 13 | — | — | >10,000 | 27 ± 2 |

Not all cell line/drug combinations were measured. Unmeasured combinations are shown as "—."

Photodoxazolidine R=H is Highly Cell Permeable:

Using MDA-MB-231 breast carcinoma cells, the cellular uptake of photodoxazolidine and azido-PEG-photodoxazolidine was analyzed by flow cytometry and compared against the uptake of doxorubicin. The results demonstrated that incubation of the cells with photodoxazolidine results in a rapid increase in cellular fluorescence, indicating that the drug is rapidly taken up into the cytosol or the plasma membrane. In contrast, azido-PEG-photodoxazolidine displays only marginally improved uptake over doxorubicin, despite the lack of charge at physiological pH. These data may help explain the similarity of the two drugs with respect to their cytotoxic activity when activated by near UV light, even though azido-PEG-photodoxazolidine exhibits a quantum yield between 5- and 10-fold higher than photodoxazolidine.

Figure 2:
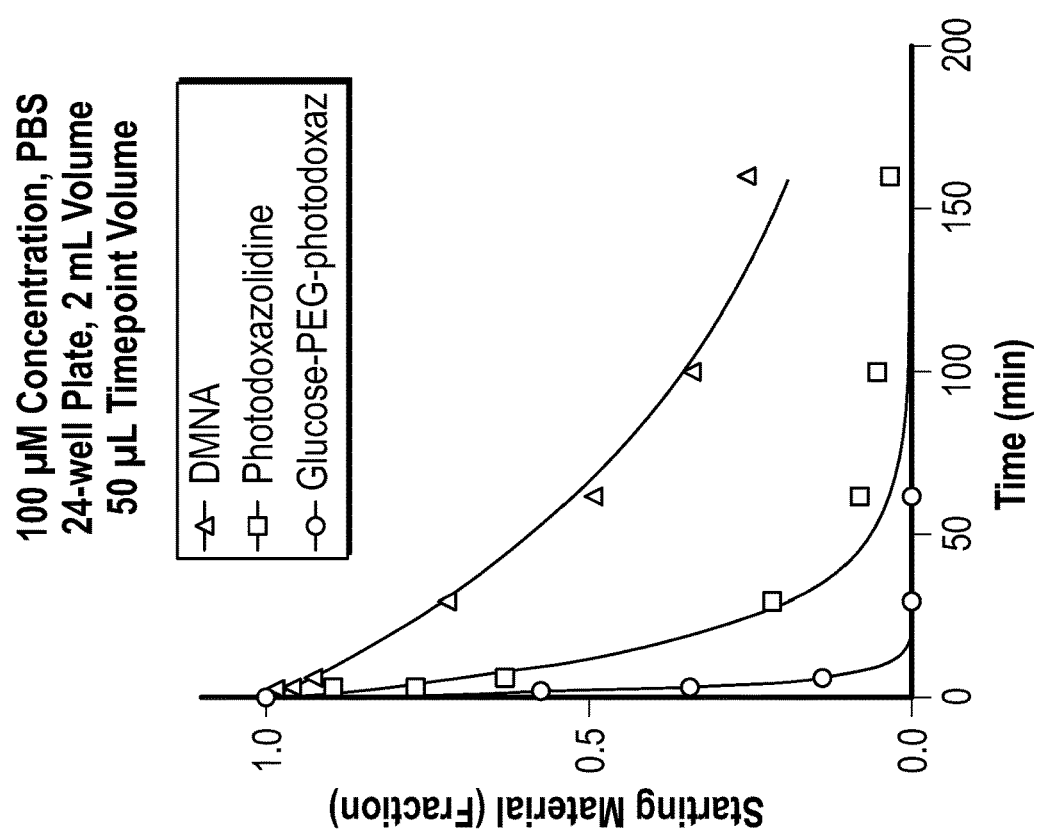
FIG. 2 shows the kinetics of irradiation of compounds of this disclosure in different solvents. Photodoxazolidine R=H, glucose-PEG-photodoxazolidine, and DMNA (4,5-dimethoxy-2-nitrobenzylalcohol) starting material, were irradiated at 100 µM in either PBS (left) or 1:1 acetonitrile:$H_2O$ (right) with near UV light (principal emission 350 nm).
Figure 2:
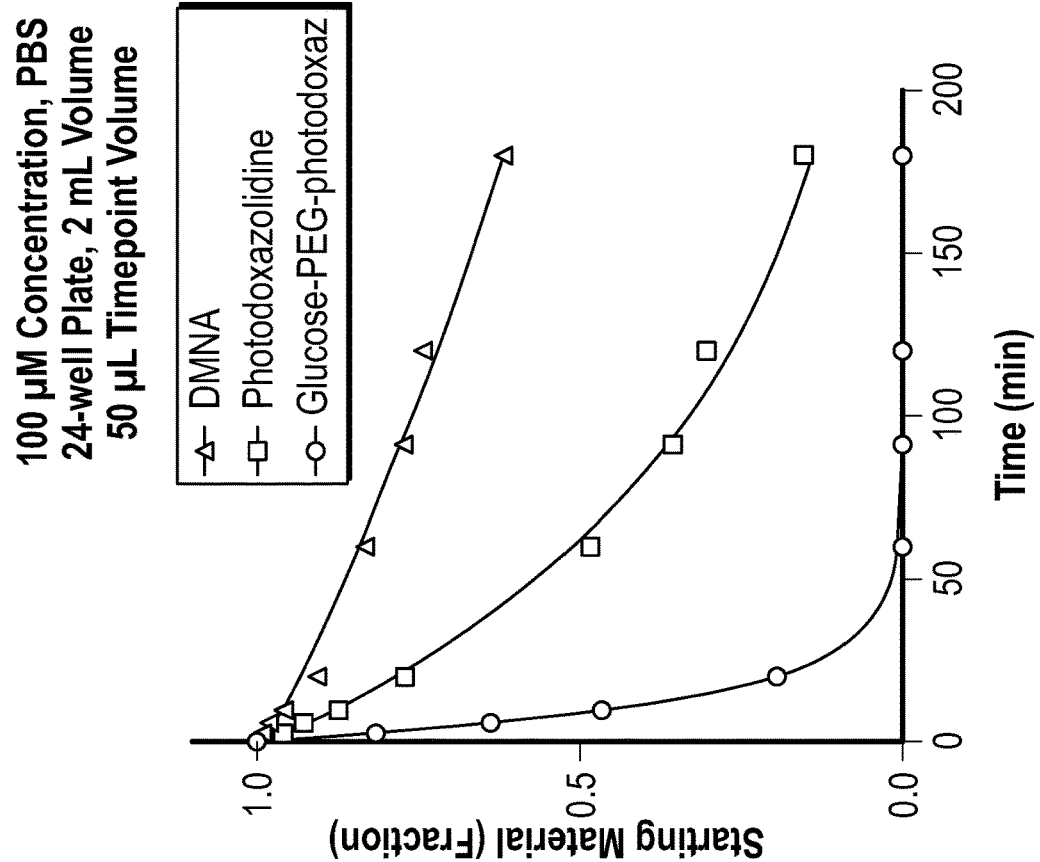

Photochemical Kinetics Suggest Intermolecular Quenching:

The measured quantum yield of 0.002 for photodoxazolidine R=H (above) was lower than expected, which raised the possibility that the presence of the anthraquinone ring complex in the prodrugs was inhibiting photocleavage by quenching the activated state. To test whether this, the irradiation kinetics of DMNA (4, 5-dimethoxy-2-nitrobenzyl alcohol) was compared against photodoxazolidine R=H, which contains the DMNA unit as the photoactivating group. Additionally, glucose-PEG-photodoxazolidine was included for comparison; a synthetic precursor to this compound, azido-PEG-photodoxazolidine, is suspected of having a quantum yield of 0.01-0.02, which is 5-10-fold larger than photodoxazolidine. Irradiation was performed in 24-well cell culture dishes using the cell culture irradiation system described above with the soft-glass high-pass filter. Initially, the irradiation solvent was PBS but was changed to 1:1 acetonitrile:water (ACN:H$_2$O) due to poor solubility of photodoxazolidine in PBS. In both solvent conditions, there were significantly different rates of the photochemical reactions (FIG. 2 and Table 3) and for all drugs, the more organic solvent system resulted in relative rates that were 2.9±0.3 times faster than those observed in PBS. In both cases, photodoxazolidine was the slowest to produce dox from the irradiation. In line with its quantum yield, glucose-PEG-photodoxazolidine reacted 4-5-fold faster than photodoxazolidine. However, DMNA was by far the fastest to undergo photochemistry in this system, converting to product approximately 30-fold faster than photodoxazolidine. Given that DMNA and photodoxazolidine both utilize the same photoactive structure, these results show that the proximity of doxazolidine to the site of photochemistry results in some quenching of the nitrophenyl chromophore excited state and significantly reduces the quantum yield of photocleavage with respect to release of doxazolidine from these prodrugs.

TABLE 3

Relative rate constants for photocleavage of photodoxazolidine R=H, glucose-PEG-photodoxazolidine, and DMNA.

| | k (min$^{-1}$) in PBS (Fold over photodoxazolidine) | k (min$^{-1}$) in ACN: H$_2$O (Fold over photodoxazolidine) |
|---|---|---|
| Photodoxazolidine | 0.0026 (1.0) | 0.0069 (1.0) |

TABLE 3-continued

Relative rate constants for photocleavage of photodoxazolidine
R=H, glucose-PEG-photodoxazolidine, and DMNA.

|  | k (min$^{-1}$) in PBS (Fold over photodoxazolidine) | k (min$^{-1}$) in ACN: H$_2$O (Fold over photodoxazolidine) |
|---|---|---|
| Glucose-PEG-photodoxazolidine | 0.011 (4.2) | 0.036 (5.2) |
| DMNA | 0.081 (31) | 0.21 (30) |

In Vivo Evaluation of Photodoxazolidine R=H:

Nude mice were injected with two million human luciferase-positive MDA-MB-231 cancer cells into a right mammary fat pad of 13 mice, and tumors were allowed two weeks to grow. The mice in the treatment group (n=5) were given 350-500 μCi of 2-deoxy-2-$^{18}$fluoroglucose (18-FDG) ip followed by iv photodoxazolidine 40 min later at 4 mg/kg (doxorubicin equivalent weight). Toxicity was indicated by body weight change. Photodoxazolidine was activated by Cherenkov radiation from prior ip administration of the 18-FGD. The mice in control group 1 (n=4) were given doxorubicin iv at 4 mg/kg and the mice in control group 2 were given 18-FDG ip followed by saline iv 40 min later. Cherenkov luminescence together with PET images of the mice on the first day of treatment confirmed the presence of the Cherenkov radiation at the tumor. After the initial two weeks, mice were treated weekly for 6 weeks.

Figure 3:
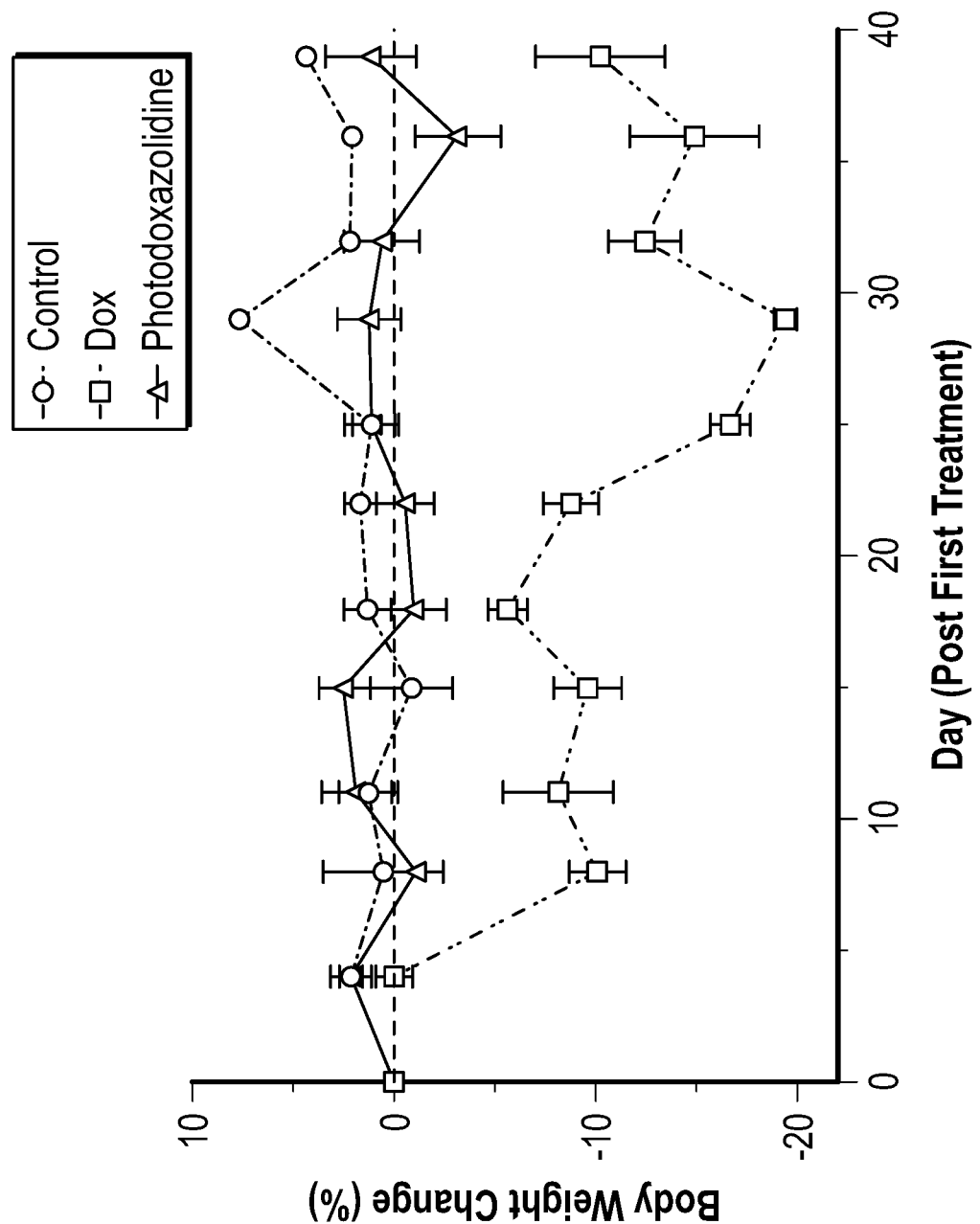
FIG. 3 shows the body weight change in mice bearing orthotopic MDA-MD-231 human breast tumor xenografts treated with doxorubicin and photodoxazolidine R=H compared with vehicle as an indication of treatment toxicity.

Body weight was measured regularly and no significant change occurred in the treatment group (p<0.0992) or the vehicle control group. However, the doxorubicin control group experienced significant weight loss over the course of the experiment (p<0.0001) as shown in FIG. 3. The stability of the treatment group's weight relative to doxorubicin group's weight indicates that photodoxazolidine is less toxic than the doxorubicin at equivalent dosing.

Figure 4:
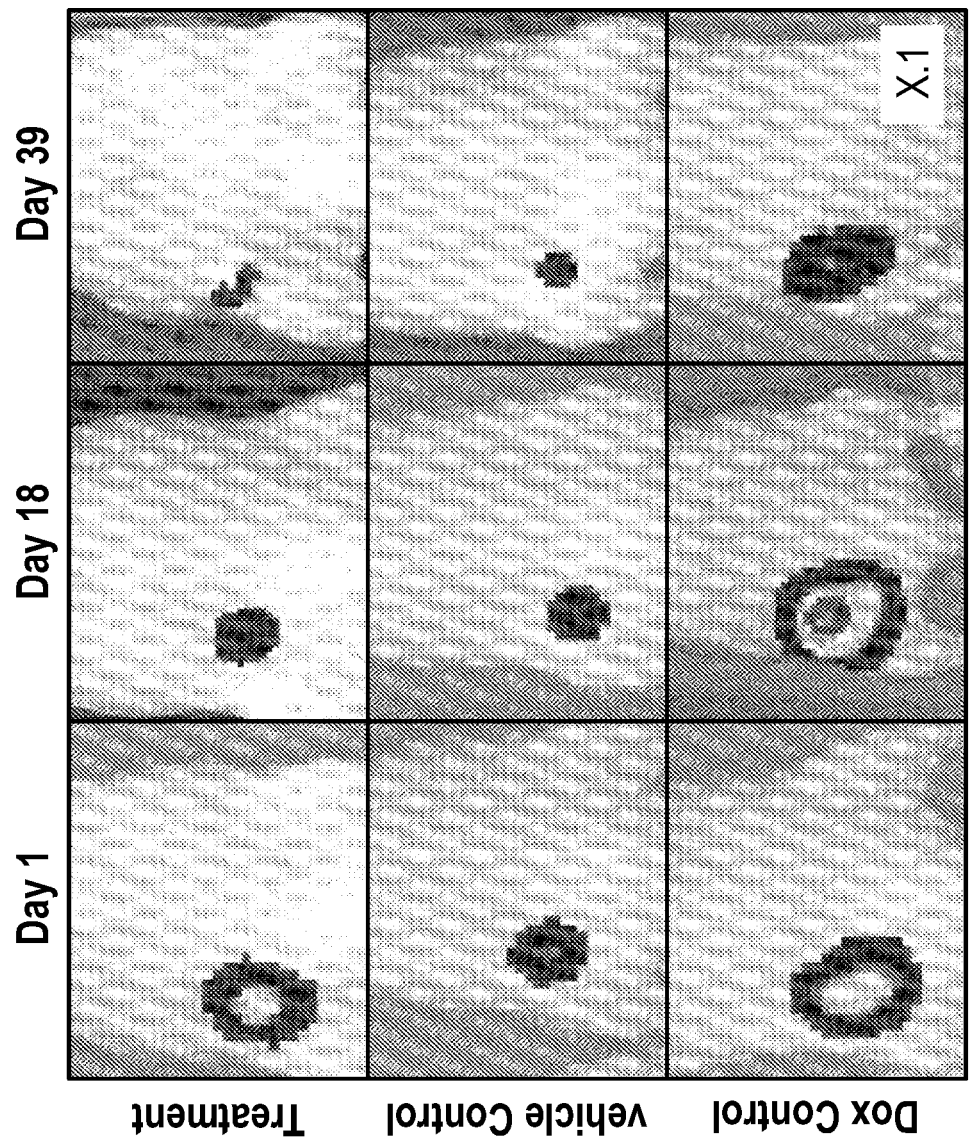
FIG. 4 shows bioluminescence images of mice with orthotopic breast tumors treated with photodoxazolidine R=H (treatment), doxorubicin, or vehicle (control). The image parameters for minimum and maximum radiance were standardized within a group ("x.1" (lower right) indicates that the parameters for this image have been lowered by a factor of ten).

Tumor size was measured from the tumor bioluminescence after injection of luciferin as shown in FIG. 4. 2 mice showed significant reductions in tumor bioluminescence.

Example 3: Synthesis and Testing of Azido-PEG-photodoxazolidine

Figure 5:
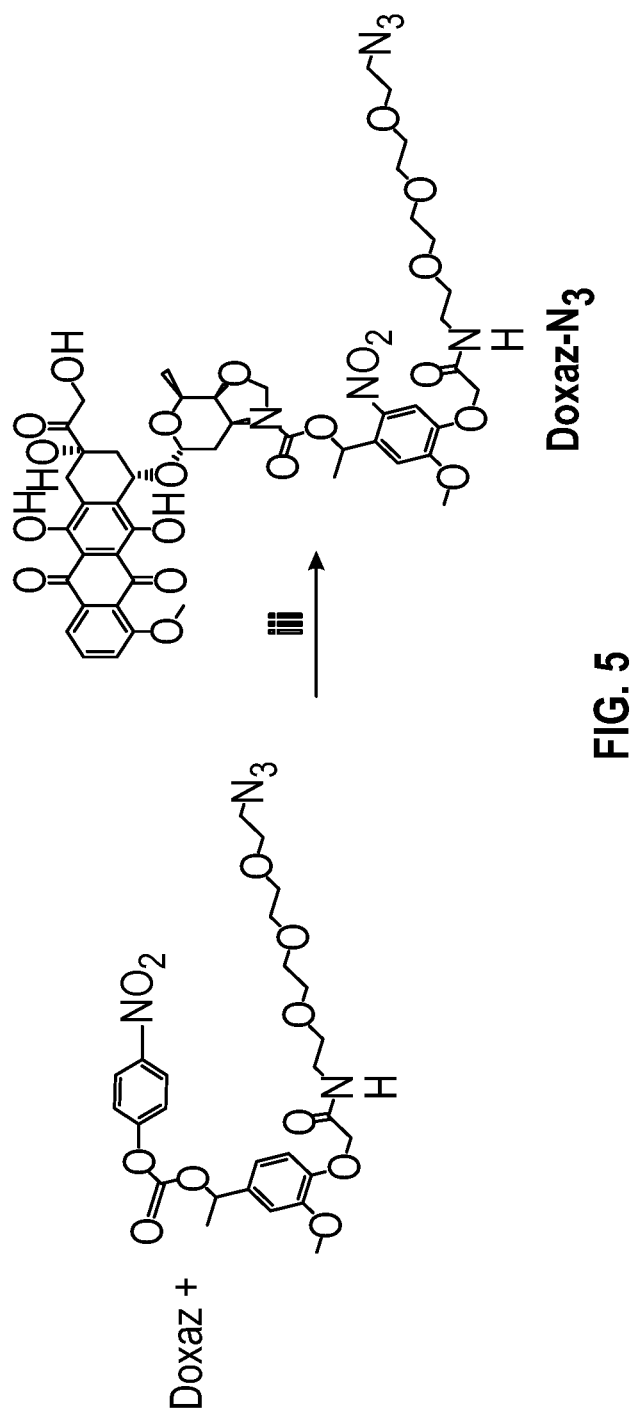
FIG. 5 shows part of the chemical synthesis scheme for azido-PEG-photodoxazolidine.
Figure 6A:
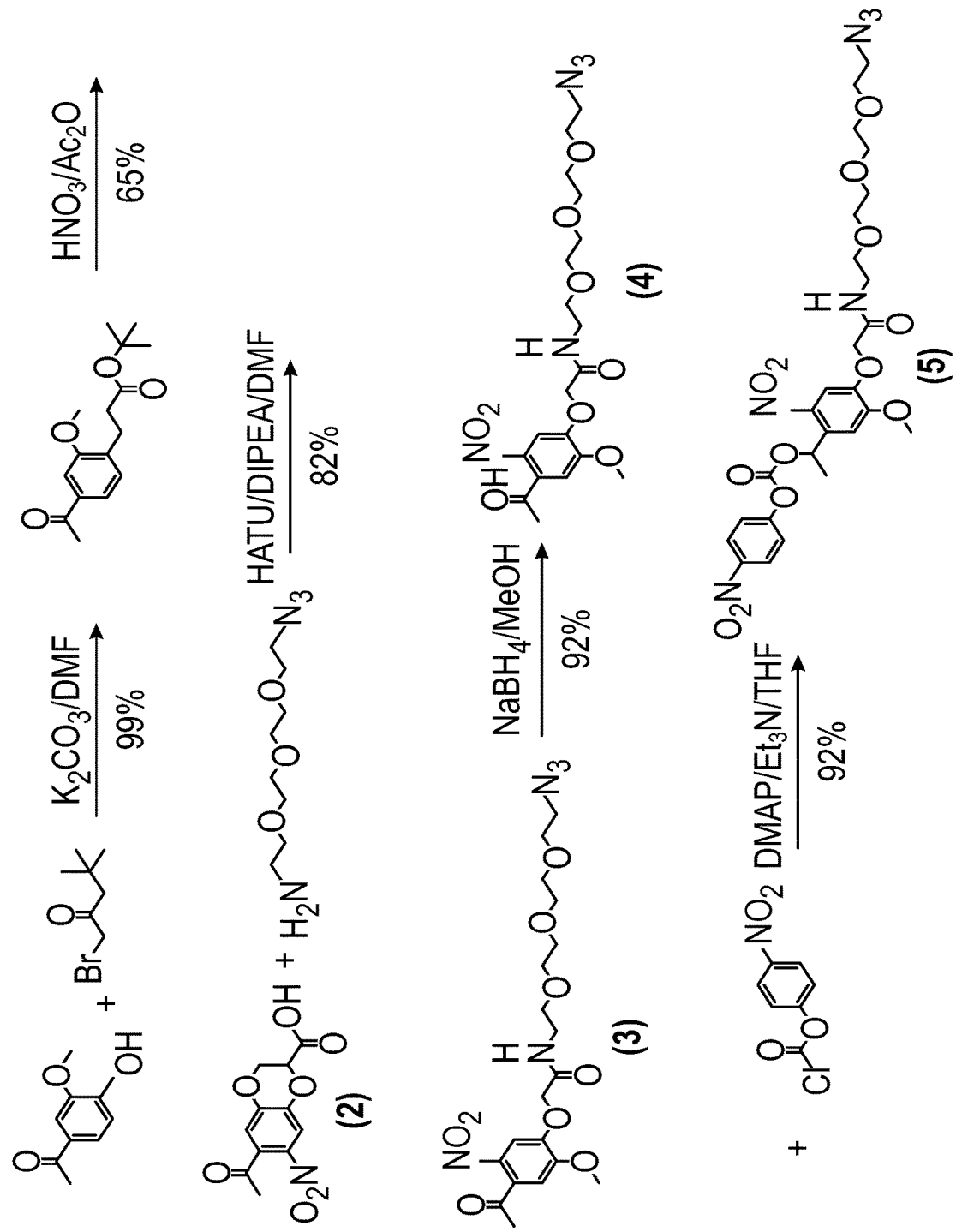
FIGS. 6A-6D show steps in the chemical synthesis scheme for MARCKS-PEG-photodoxazolidine.
Figure 6B:
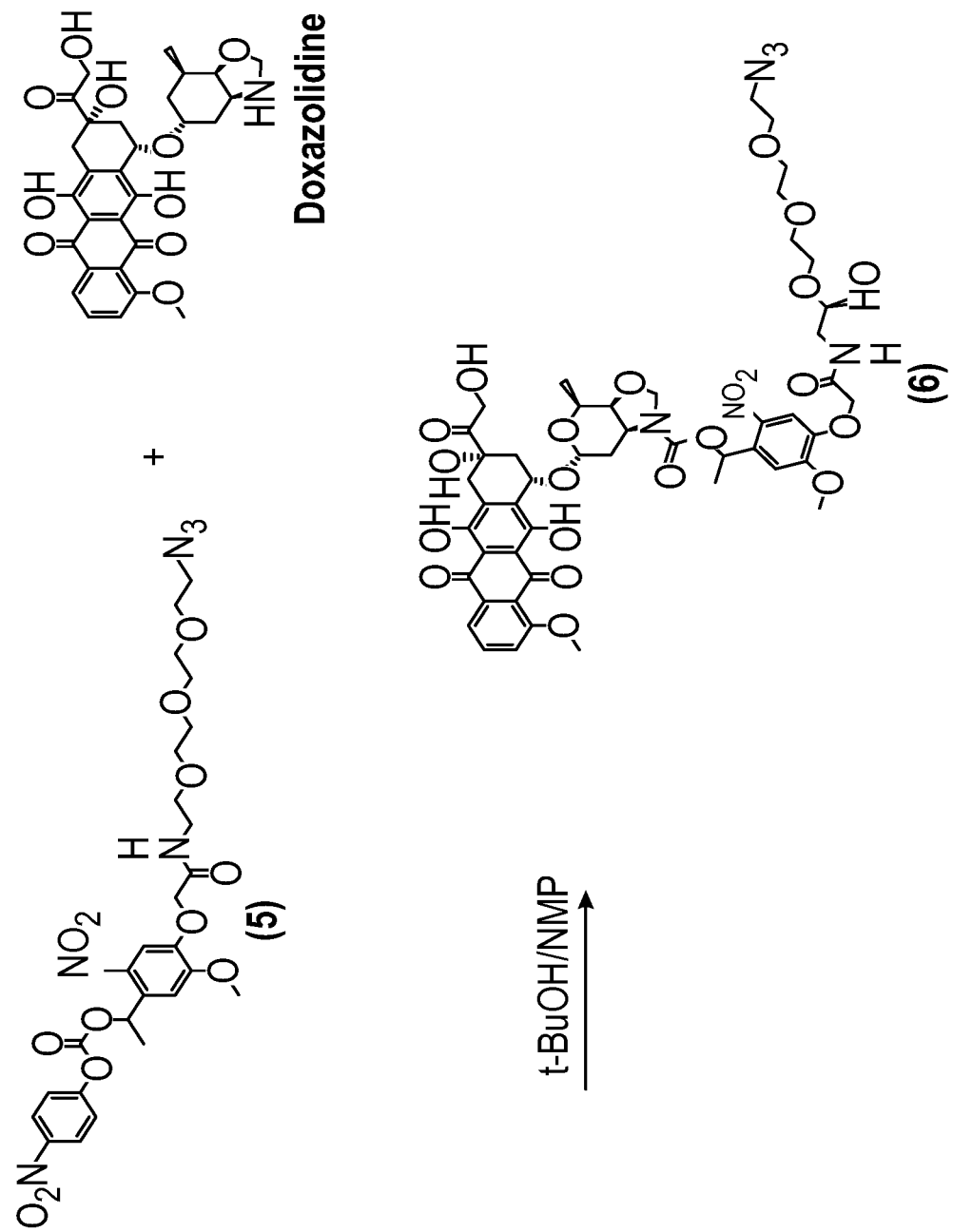
Figure 6C:
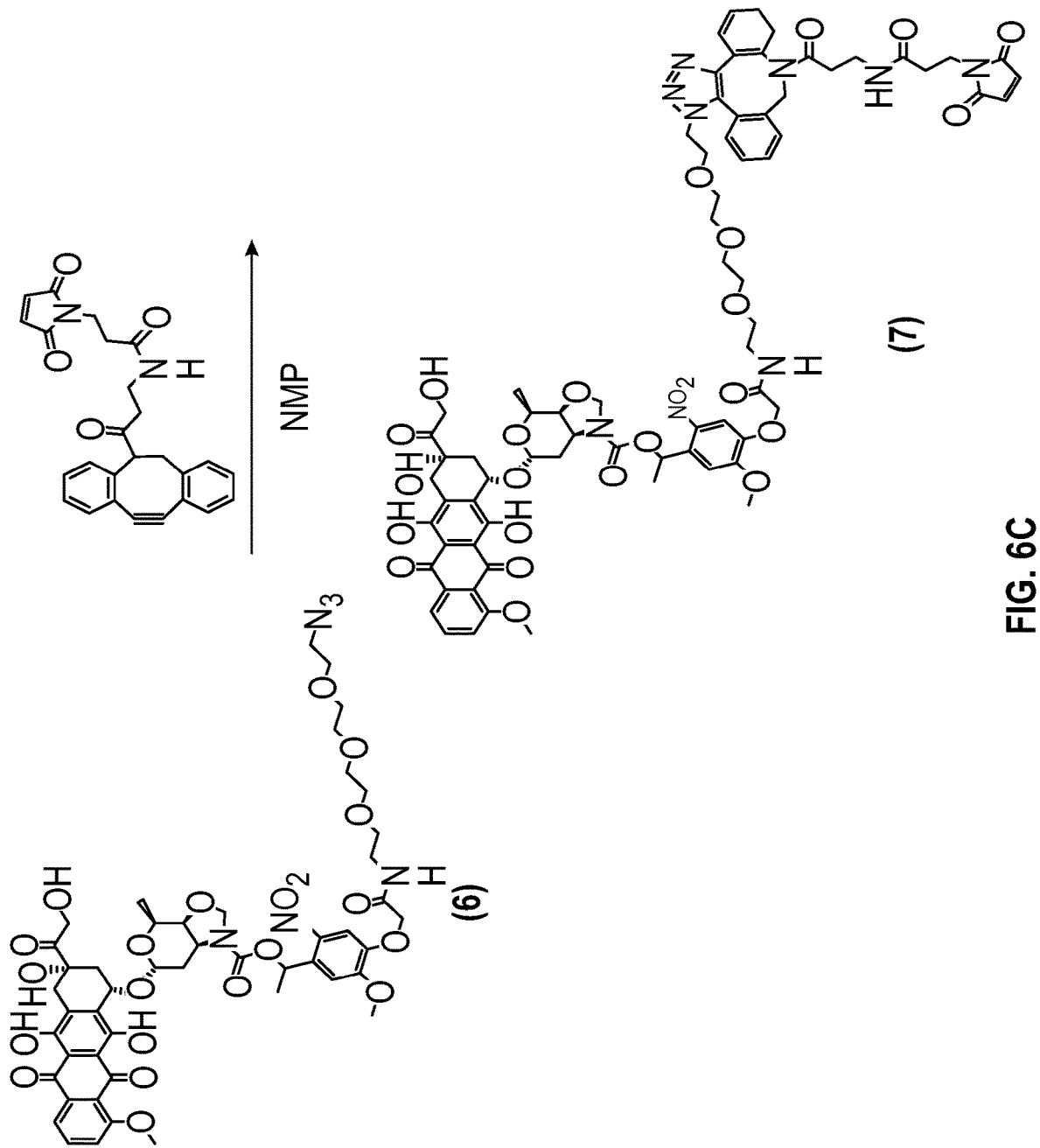
Figure 6D:
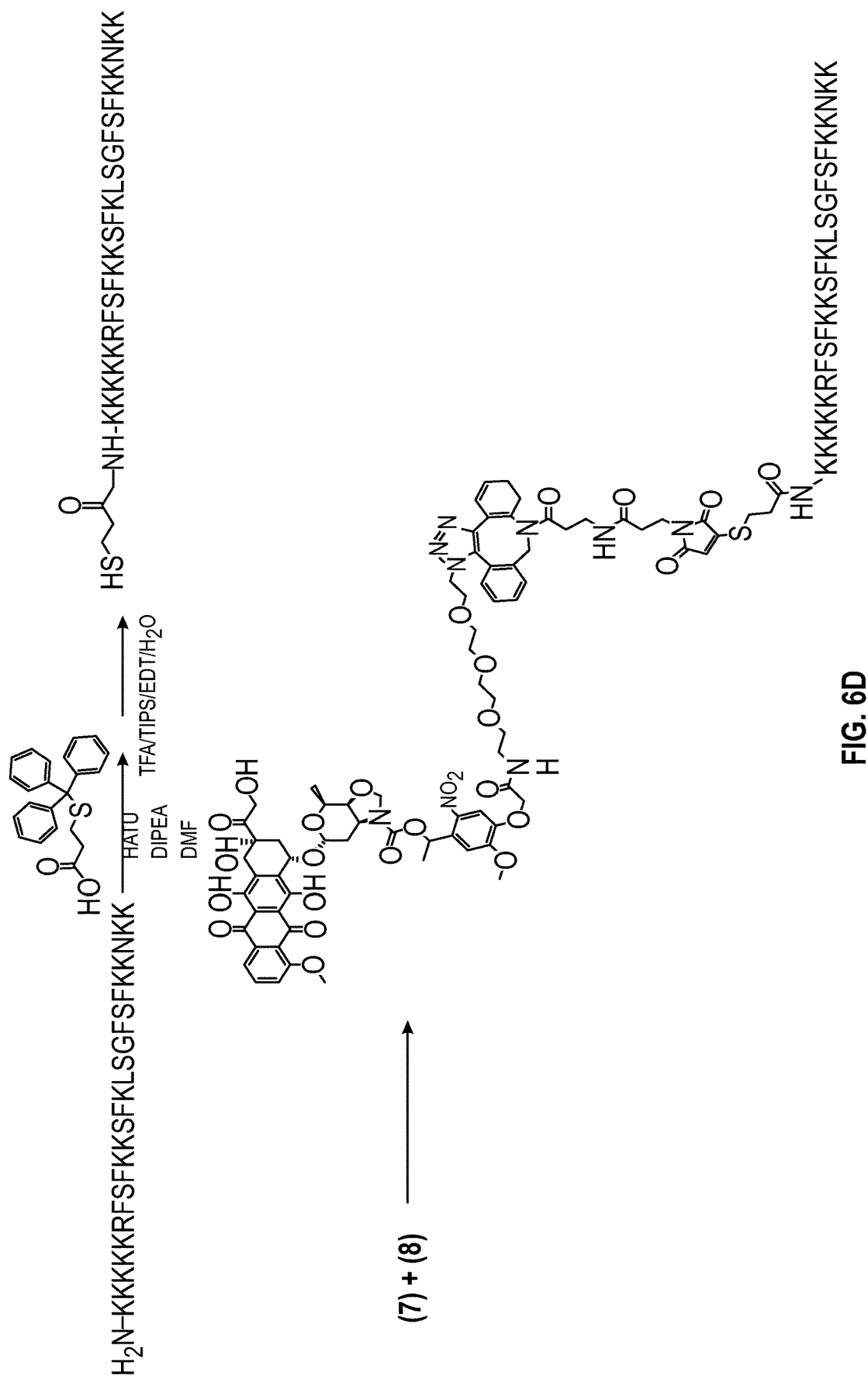

Doxazolidine (Doxaz; 0.075 mmol, 1 equiv.) and 2 equiv. of photolabile linker and HOBt (0.150 mmol) were used to synthesize azido-PEG-photodoxazolidine (chemical synthesis scheme shown in FIG. 5; photolabile linker is compound "1", azido-PEG-photodoxazolidine is "Doxaz-N$_3$"). Each reactant was dissolved in 1 mL N-Methyl-2-pyrrolidone (NMP). Molecular sieves were added to the linker solution, followed by step-wise addition of HOBt. The resulting mixture was stirred for 15 min at RT, after which Doxaz was added. The reaction was stirred overnight at RT and its progress was monitored with NMR.

Carbamoylation was used to generate azido-PEG-photodoxazolidine, a carbamate derivative that is stable in aqueous conditions. Due to the stable para-nitrophenol leaving group of the photolabile linker (FIG. 5; compound 1), its attachment to Doxaz was a facile reaction that did not create significant potential for undesired side reactions nor did it require addition of harsh reagents. The linker contained a 3-PEG spacer, which was inserted to increase the construct's hydrophilicity and couple the caged linker to the terminal azide.

Identity of azido-PEG-photodoxazolidine was ensured via 1H-NMR: (400 MHz, CHCl$_3$) δ 13.96 (1H, s, Ar-OH), 13.24 (1H, s, Ar-OH), 8.08 (1H, d, 1), 7.79 (1H, s, 2), 7.61 (1H, s, Ar), 7.44 (1H, d, 3), 7.03 (1H, t, NH), 7.00 (1H, s, Ar), 6.48 (1H, q, Bn), 5.49 (1H, t, 1'), 5.32 (1H, t, 7), 5.05 (2H, s, ox), 4.75 (2H, d, 14), 4.67 (1H, s, 9-OH), 4.52 (2H, s, —CH2-), 4.16 (1H, q, 5'), 4.12 (1H, q, 4'), 4.10 (3H, s, 4-OMe), 4.04 (1H, dt, 3'), 3.91 (3H, t, PEG), 3.67 (9H, t, PEG), 3.66 (3H, s, Ar-OMe), 3.55 (2H, t, PEG), 3.34 (2H, t, PEG), 3.27 (1H, dt, 10), 3.07 (1H, dd, 10), 2.96 (1H, t, 14-OH), 2.48 (1H, dt, 8), 2.20 (1H, dd, 8), 1.69 (3H, d, Bn-CH$_3$), 1.38 ppm (3H, d, 5'-Me). Product analysis was performed with HPLC: flow rate, 1 mL/min; eluent A=Potassium Phosphate Monobasic Buffer, pH 4.6 and eluent B=HPLC grade ACN; gradient, 80:20 A/B at 0 min to 25:75 A/B at 55 min, isocratic to 65 min, back to 80:20 A/B at 70 min, isocratic to 80 min. Eluent was monitored at 210 nm, 254 nm, 280 nm and 480 nm.

Phenolic peaks at 13.96 and 13.24 ppm indicate that the Doxaz moiety was not degraded during the reaction and that the phenolic hydrogens did not undergo an undesired side reaction. Also, presence of the 'ox' peak (5.05 ppm) verifies that Doxaz did not hydrolyze back to Doxorubicin (Dox).

Manifestation of azido-PEG-photodoxazolidine was confirmed by analytical HPLC which revealed two peaks for the azides, with retention time of 39 min. These are the two diastereomers, which result from the benzylic stereocenter (marked with an asterisk in FIG. 5).

Removing this methyl would not interrupt the photodissociation. However, the presence of the methyl gives rise to a tertiary carbon radical in the photochemical mechanism, hence stabilizing the intermediate more than that of an otherwise secondary carbon radical. Stereochemistry should be irrelevant to the photodissociation mechanism.

Quantum Yield:

Concentration of azido-PEG-photodoxazolidine was determined via absorbance (λ=480 nm, ε=11500 M$^{-1}$ cm$^{-1}$). A sample (0.39 mol) was dissolved in 1 mL of ACN and transferred to a cuvette. A 12.4 mW Omnichrome HeCd was used to irradiate the solution for 30 min at 325 nm. Aliquots of 10 μL were collected at different times and analyzed by HPLC to determine the % Dox in relation to that of azido-PEG-photodoxazolidine. In calculating quantum yield: power (without cuvette)=12.4 mW, (with cuvette) =10.7 mW, incident light=11.55 mW; energy=0.462 J, 7.55× 1017 photons; t=40 sec when % Dox=9.2. Experiments were performed in triplicate.

Azido-PEG-photodoxazolidine was irradiated with a 12.4 mW monochromatic laser at 325 nm for 30 min. Aliquots were collected throughout to determine the amount of azido-PEG-photodoxazolidine in relation to released doxorubicin, which was quantified by HPLC. At the 40 sec time increment, 9.2% of doxorubicin was released; this data point was used to calculate the quantum yield. The average of triplicate quantum yield experiments was 0.025. This value is in the low end of the quantum yield range, yet is beneficial because it signifies that UV must be applied for longer durations prior to release of the cytotoxic agent. This makes administration of this photo-activated prodrug safer, and its synthesis more practical.

Example 4: Synthesis of MARCKS-PEG-Photodoxazolidine

Reagents and Instrumentation: All chemicals were purchased from Sigma-Aldrich (St. Louis, Mo.) unless otherwise noted. MEM, FBS, penicillin/streptomycin and trypsin-EDTA were purchased from Thermo Fisher Scientific (Waltham, Mass.). Doxazolidine/Doxoform was synthesized from doxorubicin free base derived from lactose-containing clinical preparations of doxorubicin hydrochloride as previously described (Barthel, et al., J Med Chem 2012, supra). All peptides were synthesized by Fmoc solid phase peptide chemistry using CEM Liberty Microwave Peptide Synthesizer (Matthews, N.C.). The H-Rink-Amide-Chem matrix resin with a loading capacity of 0.45 mmol/g was purchased from PCas BioMatrix Inc (Quebec Canada) and all amino acids were purchased from ChemPep (Wellington, Fla.). NMR spectra were acquired on a Bruker AV-III 400 MHz NMR Spectrometer (Billerica, Mass.) or Varian INOVA 400 MHz NMR spectrometer (Santa Clara, Calif.). Spectra were analyzed with MestReNova software (Santiago de Compostela, Spain). Chemical shifts are reported in parts per million (ppm) on δ scale and standardized to the residual solvent peak. ESI-MS analysis was performed using Waters Synapt G2 Qtof (Milford, Mass.). Concentrations of all doxazolidine-containing compounds were measured by absorbance at 480 nm using an extinction coefficient of 11,500 $M^{-1}cm^{-1}$. Reverse phase HPLC was performed with an Agilent Technologies 1200 Series instrument, Hewlett Packard 1090 instrument or Varian Prostar/Rainin Dynamax preparative HPLC system. Analytical HPLC was performed using the C18 150×4.6 mm column, eluting at 1 mL/min. Semi-preparative HPLC was performed using the C18 250×10 mm column, eluting at 3 mL/min. Preparative HPLC was performed using C18 300×21 mm column, eluting at 10 ml/min. The mobile phase at t=0 is 80% potassium phosphate buffer (15 mM, pH=4.6) or 0.1% TFA in water, and 20% acetonitrile. Acetonitrile was increased 1%/min until it reaches 80%. The 96 well plates were read with a Beckman Coulter DTX 880 Multimode Detector (Indianapolis, Id.) and GraphPad Prism software (La Jolla, Calif.) was used to calculate $IC_{50}$ values.

Synthesis of MARCKS-PEG-Photodoxazolidine (FIGS. 6A-6D)

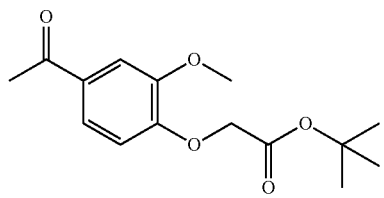 [SMILES: COc1cc(C(C)=O)ccc1OCC(=O)OC(C)(C)C]

Compound 1:

Acetovanillone (10 g, 60.18 mmol) and potassium carbonate (13.31 g, 96.29 mmol) were combined and dissolved in DMF (80 ml). t-Butyl bromoacetate (14.09 g, 10.66 ml, 72.22 mmol) was added slowly at 0° C. The resulting mixture was stirred overnight. The reaction was poured over water and the aqueous solution was extracted with ethyl acetate. The combined organic phase was washed with brine, dried with sodium sulfate and evaporated to give 16.75 g (99%) as a white solid. 1H NMR (400 MHz, chloroform-d) δ 7.57-7.50 (m, 2H), 6.77 (d, J=8.3 Hz, 1H), 4.66 (s, 2H), 3.94 (s, 3H), 2.57 (s, 3H), 1.47 (s, 9H).

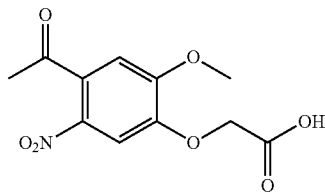 [SMILES: COc1cc(C(C)=O)c([N+](=O)[O-])cc1OCC(=O)O]

Compound 2:

Compound 1 (5 g) in acetic anhydride (15 ml) was added to a solution of 70% nitric acid (15 ml) and acetic anhydride (10 ml) at 0° C. The mixture was stirred at 0° C. for 2 hours followed by stirring at room temperature for 4 hours. The reaction was poured over water and chilled at 4° C. overnight. The precipitates were filtered and recrystallized with water to yield 3.14 g (65%) as a solid. 1H NMR (400 MHz, Methanol-d4) δ 7.64 (s, 1H), 7.08 (s, 1H), 4.83 (s, 2H), 3.98 (s, 3H), 2.51 (s, 3H).

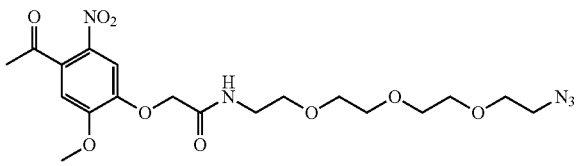 [SMILES: COc1cc(C(C)=O)c([N+](=O)[O-])cc1OCC(=O)NCCOCCOCCOCCN=[N+]=[N-]]

Compound 3:

Compound 2 (1.12 g, 4.17 mmol) and HATU (3.17 g, 8.33 mmol) were dissolved in DMF (20 mL). DIPEA (1.08 g, 1.45 ml, 8.33 mmol) was added and the mixture was stirred at room temperature for 5 min. Then 11-azido-3,6,9-trioxaundecan-1-amine (1 g, 4.58 mmol) was added, and the resulting mixture was stirred at room temperature overnight. Ethyl acetate was poured onto the reaction mixture. The solution was washed with water and brine, dried with sodium sulfate, and the solvent rotary evaporated. The crude mixture was purified by silica gel flash column chromatography. The fractions were collected and solvent evaporated to yield 1.16 g of compound 3 (82%) as a solid. 1H NMR (400 MHz, DMSO-d6) δ 8.11 (t, J=6.0 Hz, 1H), 7.61 (s, 1H), 7.26 (s, 1H), 4.69 (s, 2H), 3.95 (s, 3H), 3.63-3.48 (m, 10H), 3.44 (d, J=5.6 Hz, 2H), 3.41-3.35 (m, 2H), 3.33 (s, 2H), 3.29 (d, J=5.7 Hz, 2H), 2.52 (s, 3H).

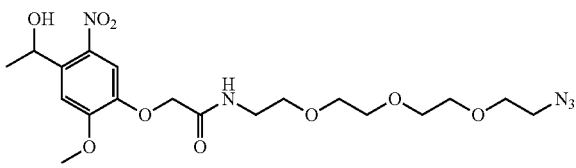 [SMILES: COc1cc(C(C)O)c([N+](=O)[O-])cc1OCC(=O)NCCOCCOCCOCCN=[N+]=[N-]]

Compound 4:

Compound 3 (0.53 g, 1.13 mmol) was dissolved in MeOH (5 ml). To this solution, sodium borohydride (0.128 g, 3.39 mmol) was added slowly at 0° C. The resulting solution was warmed to room temperature and stirred for 1 h. After the solvent was evaporated, water and 1 mL of 5% HCl were added. The solution was extracted with ethyl acetate. The combined organic phase was washed with brine, dried with sodium sulfate and the solvent rotary evaporated to give 0.491 g (92%) as a solid. 1H NMR (400 MHz, DMSO-d6) δ 8.07 (t, J=5.8 Hz, 1H), 7.52 (s, 1H), 7.39 (s, 1H), 5.52 (d, J=4.5 Hz, 1H), 5.33-5.21 (m, 1H), 4.60 (s, 2H), 3.93 (s, 3H), 3.62-3.48 (m, 9H), 3.47-3.36 (m, 5H), 3.28 (q, J=5.8 Hz, 2H), 1.36 (d, J=6.2 Hz, 3H).

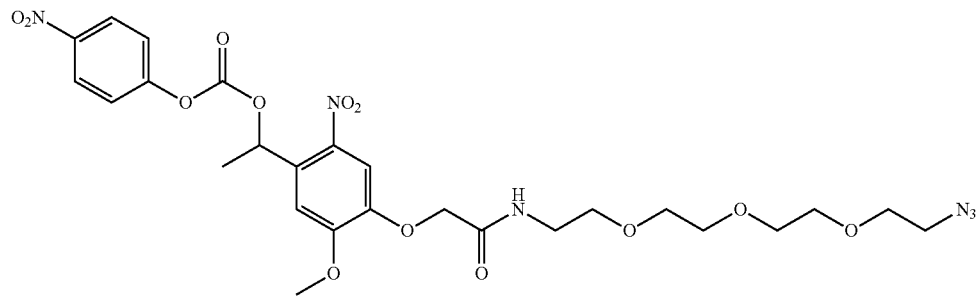 [SMILES: COc1cc(C(C)OC(=O)Oc2ccc([N+](=O)[O-])cc2)c([N+](=O)[O-])cc1OCC(=O)NCCOCCOCCOCCN=[N+]=[N-]]

Compound 5:

Compound 4 was dissolved in THF (3.75 ml). 4-Nitrophenyl chloroformate, triethyl amine and DMAP were added, and the resulting mixture was stirred at room temperature for 18 h. Ethyl acetate was poured onto the reaction mixture. The solution was washed with water and brine, dried with sodium sulfate, and the solvent rotary evaporated. The crude mixture was purified by silica gel flash column chromatography. The fractions were collected and evaporated to yield 0.159 g of compound 5 (63%) as a solid. 1H NMR (400 MHz, DMSO-d6) δ 8.33-8.26 (m, 2H), 8.11 (t, J=5.7 Hz, 1H), 7.57 (s, 1H), 7.56-7.50 (m, 2H), 7.23 (s, 1H), 6.28 (q, J=6.4 Hz, 1H), 4.65 (s, 2H), 3.98 (s, 3H), 3.60-3.35 (m, 15H), 3.29 (dd, J=6.2, 5.2 Hz, 2H), 1.72 (d, J=6.4 Hz, 3H).

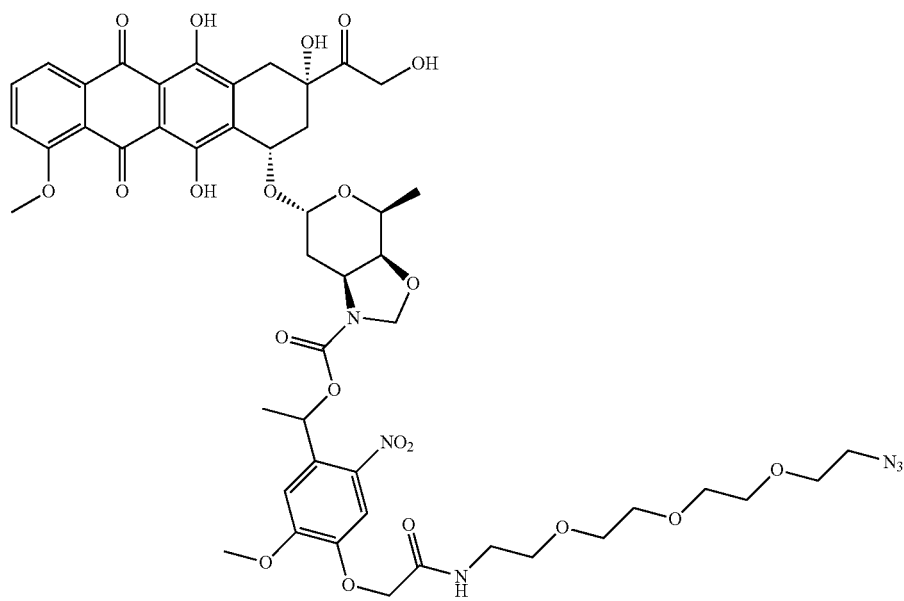 [SMILES: COc1cc(C(C)OC(=O)N2CO[C@@H]3[C@H](C)O[C@@H](O[C@H]4C[C@](O)(C(=O)CO)Cc5c(O)c6c(c(O)c54)C(=O)c4c(OC)cccc4C6=O)C[C@@H]32)c([N+](=O)[O-])cc1OCC(=O)NCCOCCOCCOCCN=[N+]=[N-]]

Compound 6:

Compound 5 (0.047 g, 0.0736 mmol) and doxazolidine (0.0409 g, 0.0736 mmol) were dissolved in NMP (2 mL) with molecular sieves separately. HOBt (0.0199 g, 0.1472 mmol) was added to the solution of compound 5. After it was stirred for 15 min at room temperature, the two solutions were combined. The resulting mixture was stirred at room temperature overnight. The crude product (compound 6) was purified by preparative RP-HPLC. 1H NMR: (400 MHz, CDCl$_3$) δ 13.96 (1H, s, Ar-OH), 13.24 (1H, s, Ar-OH), 8.08 (1H, d, 1), 7.79 (1H, s, 2), 7.61 (1H, s, Ar), 7.44 (1H, d, 3), 7.03 (1H, t, NH), 7.00 (1H, s, Ar), 6.48 (1H, q, Bn), 5.49 (1H, t, 1'), 5.32 (1H, t, 7), 5.05 (2H, s, ox), 4.75 (2H, d, 14), 4.67 (1H, s, 9-OH), 4.52 (2H, s, —CH2-), 4.16 (1H, q, 5'), 4.12 (1H, q, 4'), 4.10 (3H, s, 4-OMe), 4.04 (1H, dt, 3'), 3.91 (3H, t, PEG), 3.67 (9H, t, PEG), 3.66 (3H, s, Ar-OMe), 3.55 (2H, t, PEG), 3.34 (2H, t, PEG), 3.27 (1H, dt, 10), 3.07 (1H, dd, 10), 2.96 (1H, t, 14-OH), 2.48 (1H, dt, 8), 2.20 (1H, dd, 8), 1.69 (3H, d, Bn-CH$_3$), 1.38 ppm (3H, d, 5'-Me). MS-ESI⁻, observed MH⁻ 1051.3470; calculated MH⁻ 1051.3499.

purified by preparative RP-HPLC. MS-ESI⁺, observed MH⁺1480.5135; calculated MH⁺1480.5109.

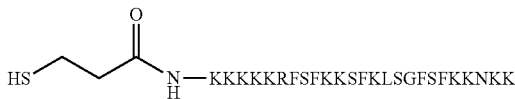

Compound 8

MARCKS-ED peptide (KKKKKRFSFKKSFKLSGFSFKKNKK (SEQ ID NO:1) (0.1 mmol) was synthesized by standard Fmoc solid phase peptide synthesis. MARCKS-ED peptide on resin (0.075 mmol), s-trityl-3-mercaptopropionic acid (0.150 mmol) and HATU were combined and dissolved in DMF (5 ml). After the solution reached a homogeneous appearance, DIPEA (0.15 mmol) was added. The resulting mixture was stirred at

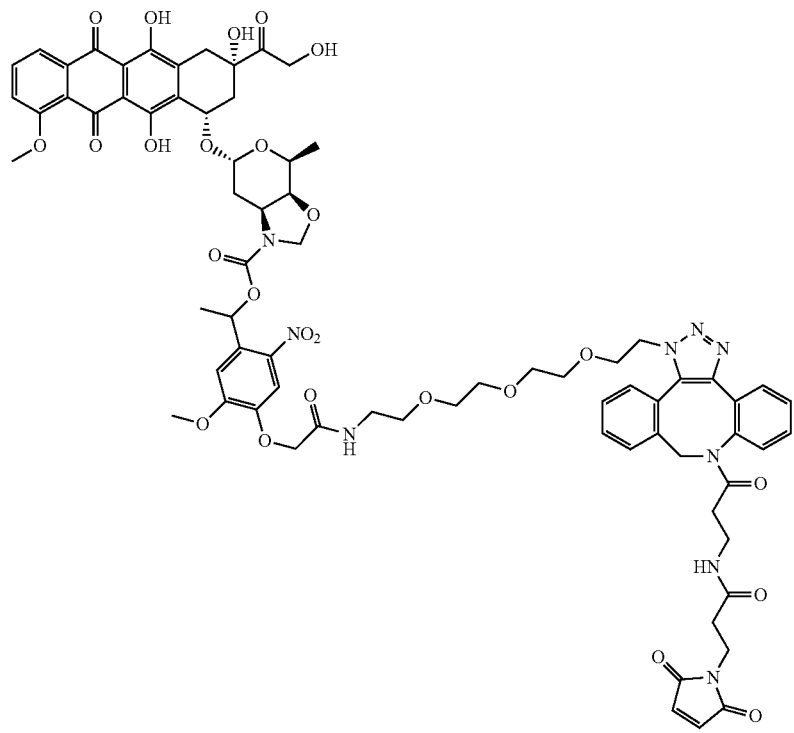 [SMILES: COc1cc(C(C)OC(=O)N2CO[C@@H]3[C@H](C)O[C@@H](O[C@H]4C[C@](O)(C(=O)CO)Cc5c(O)c6c(c(O)c54)C(=O)c4c(OC)cccc4C6=O)C[C@@H]32)c([N+](=O)[O-])cc1OCC(=O)NCCOCCOCCOCCn1nnc2c1-c1ccccc1CN(C(=O)CCNC(=O)CCN1C(=O)C=CC1=O)c1ccccc1-2]

Compound 7:

Compound 6 (0.0118 g, 11.2 μmol) was dissolved in NMP (1 ml). DBCO-maleimide (0.0096 g, 22.4 μmol) was added. The resulting mixture was stirred at room temperature overnight. DCM was poured into the reaction, followed by washing with water and brine, drying with sodium sulfate, and rotary evaporation of solvent. The crude mixture was room temperature overnight. The peptide cleavage from the resin and universal deprotection were carried out with TFA cocktail: TIPS (50 μl), H$_2$O (125 μL), EDT (125 μL), and TFA (4.7 mL). The reaction was left at room temperature for 2 h. Cold ether was added and the peptides were precipitated by centrifugation. The crude peptide was purified by semi-prep RP-HPLC.

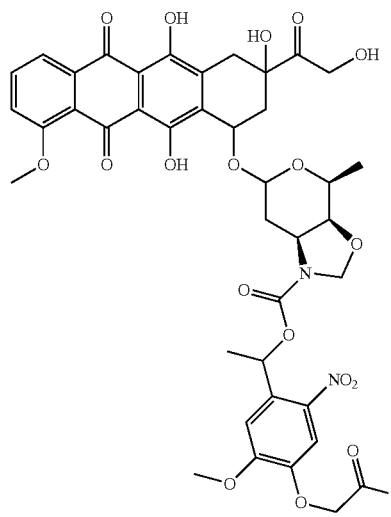
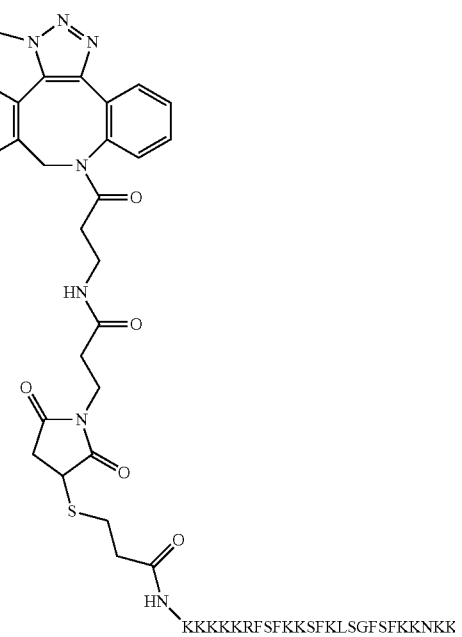

Compound 9 (MARCKS-PEG-photodoxazolidine):

MARCKS-ED peptide (SEQ ID NO:1) (compound 8, 1 μmol) was dissolved in PBS buffer under inert atmosphere, to which photodoxazolidine-maleimide (compound 7, 1 μmol) in DMF (400 μL) was added. The reaction was left under dark and inert condition at room temperature overnight. The mixture was lyophilized and purified by semiprep RP-HPLC. ESI-MS confirmed the identity of Doxaz-MARCKS (M+1=4648.34 Da). The peaks of highest intensity, 1162.85, 930.48 and 775.57 m/z, corresponded to M+4, M+5 and M+6 charged states, respectively.

Figure 7A:
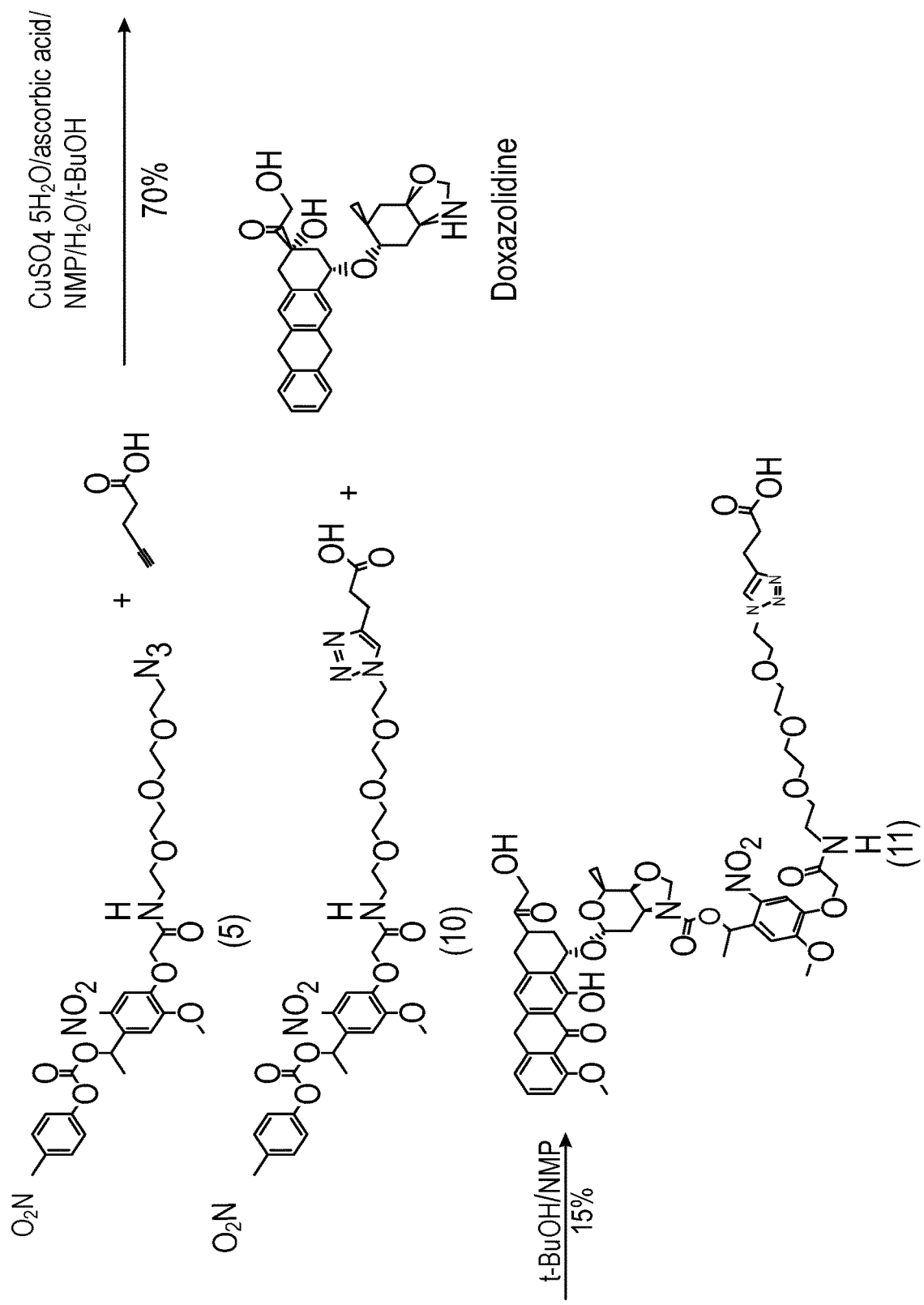
FIGS. 7A and 7B show steps in the chemical synthesis scheme for glucose-PEG-photodoxazolidine.
Figure 7B:
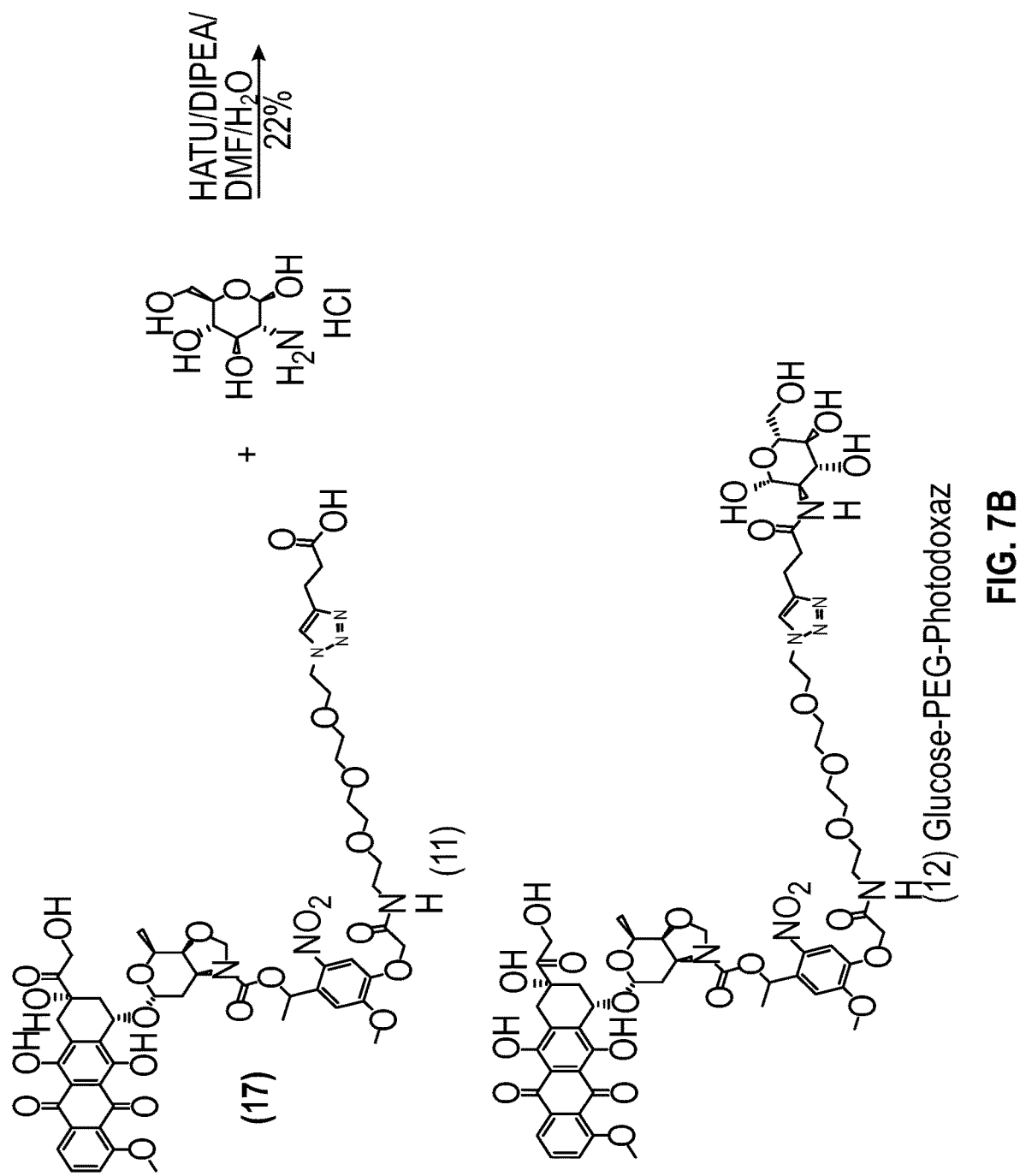

Example 5: Synthesis of Glucose-PEG-photodoxazolidine (FIGS. 7A and 7B)

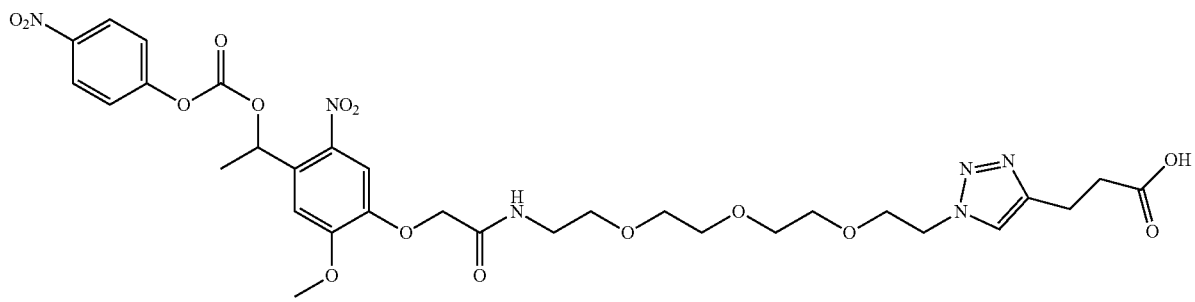 [SMILES: COc1cc(C(C)OC(=O)Oc2ccc([N+](=O)[O-])cc2)c([N+](=O)[O-])cc1OCC(=O)NCCOCCOCCOCCn1cc(CCC(=O)O)nn1]

Compound 10:

Compound 5 (0.483 g, 0.759 mmol) was dissolved in a solution of NMP (2 mL), water (1 mL) and t-butyl alcohol (1 mL). 4-Pentynoic acid (0.089 g, 0.911 mmol) and a solution of CuSO$_4$·5H$_2$O (0.0038 g, 0.0152 mmol) and sodium ascorbate (0.015 g, 0.0759 mmol) in water (1 mL) were added. The resulting mixture under an inert atmosphere was stirred at room temperature overnight. Ethyl acetate was poured over the reaction, followed by washing with water and brine, drying with sodium sulfate and rotary evaporation. The crude mixture was purified by silica gel column chromatography. The fractions were collected and evaporated to yield 0.404 g (70%) as a solid. 1H NMR (400 MHz, Chloroform-d) δ 8.26 (d, J=9.3 Hz, 2H), 7.65 (s, 1H), 7.59 (s, 1H), 7.36 (d, J=9.3 Hz, 2H), 7.16 (s, 1H), 6.53 (d, J=6.4 Hz, 1H), 4.60 (s, 2H), 4.48 (s, 2H), 4.00 (s, 3H), 3.79 (s, 2H), 3.70-3.48 (m, 11H), 3.05 (s, 2H), 2.72 (s, 2H), 1.78 (d, J=6.4 Hz, 3H).

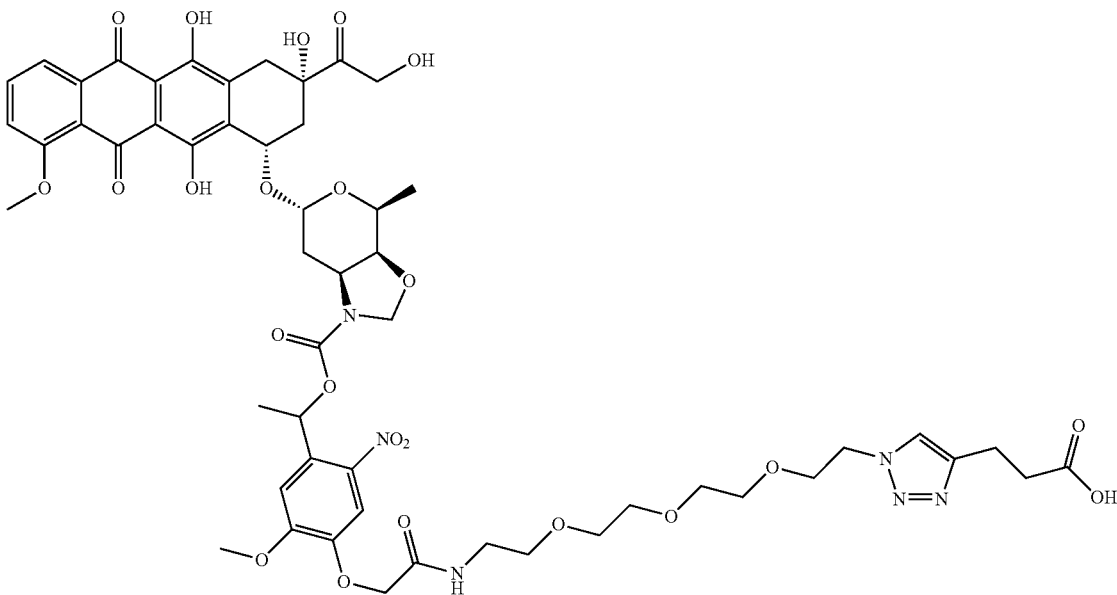 [SMILES: COc1cc(C(C)OC(=O)N2CO[C@@H]3[C@H](C)O[C@@H](O[C@H]4C[C@](O)(C(=O)CO)Cc5c(O)c6c(c(O)c54)C(=O)c4c(OC)cccc4C6=O)C[C@@H]32)c([N+](=O)[O-])cc1OCC(=O)NCCOCCOCCOCCn1cc(CCC(=O)O)nn1]

Compound 11:

Compound 10 (0.113 g, 0.148 mmol) and doxazolidine (0.041 g, 0.074 mmol) were separately dissolved in NMP (4 mL) with molecular sieves. HOBt (0.0199 g, 0.148 mmol) was added to a solution of compound 10 and the mixture was stirred at room temperature for 15 min. Then, these two solutions were combined and the resulting mixture was stirred at room temperature for 48 h. After water was poured into the reaction, it was extracted with DCM. The combined organic layer was dried with sodium sulfate and rotary evaporated. The crude mixture was purified by preparative RP-HPLC to yield 10.693 μmol (15%) of compound 11 as a red solid. 1H NMR (400 MHz, Chloroform-d) δ 13.93 (s, 1H), 13.21 (s, 1H), 8.07-7.97 (m, 1H), 7.77 (td, J=8.1, 3.1 Hz, 1H), 7.60 (s, 1H), 7.54 (s, 1H), 7.44-7.34 (m, 1H), 7.15 (s, 1H), 6.99 (d, J=8.8 Hz, 1H), 6.43 (dq, J=13.0, 6.4 Hz, 1H), 5.48 (t, J=5.2 Hz, 1H), 5.32 (s, 1H), 5.01 (s, 2H), 4.75 (d, J=3.0 Hz, 2H), 4.55 (d, J=16.6 Hz, 2H), 4.51-4.33 (m, 3H), 4.21-4.11 (m, 2H), 4.12-3.98 (m, 4H), 3.90 (s, 2H), 3.80 (t, J=5.0 Hz, 3H), 3.67-3.42 (m, 12H), 3.38-3.23 (m, 2H), 3.11-2.97 (m, 3H), 2.69 (t, J=6.8 Hz, 2H), 2.51-2.37 (m, 1H), 2.32-2.01 (m, 3H), 1.93-1.71 (m, OH), 1.65 (t, J=6.6 Hz, 3H), 1.38 (d, J=6.5 Hz, 3H). MS-ESI$^+$, observed MH$^+$1151.3949; calculated MH$^+$1151.3944.

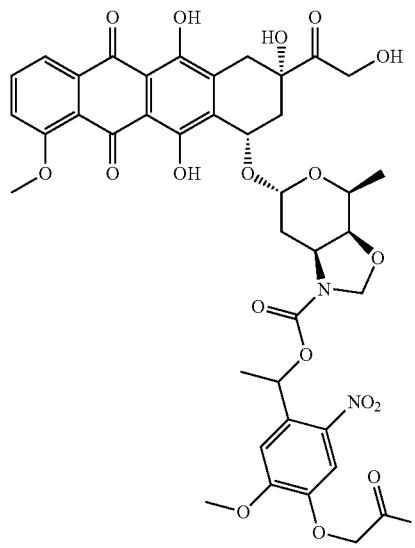

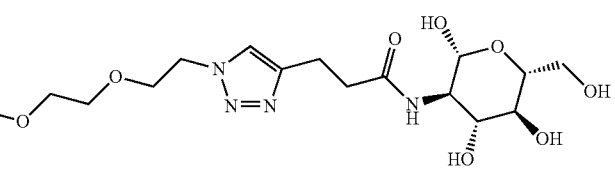

Compound 12 (Glucose-PEG-Photodoxazolidine):

Compound 11 (0.0262 g, 22.79 μmol), HATU (0.0880 g, 227.9 μmol) and DIPEA (0.0295 g, 39.7 μl, 227.9 μmol) were dissolved in DMF (4 mL). A solution of D-glucosamine·HCl (0.0491 g, 227.9 μmol) in water (800 μl) was added. The resulting mixture was stirred at room temperature for 24 h. A solution of DCM:isopropanol=3:1 was poured into the reaction mixture, which was washed by water, dried with sodium acetate and evaporated. The crude mixture was purified by preparative RP-HPLC to yield 6.64 mg (22%) of glucose-PEG-photodoxazolidine (compound 12) as a red solid. 1H NMR (400 MHz, DMSO-d6) δ 14.01 (s, 1H), 13.23 (s, 1H), 7.92 (dd, J=7.4, 2.5 Hz, 4H), 7.77 (d, J=11.7 Hz, 1H), 7.73-7.61 (m, 2H), 7.54 (s, 1H), 7.50 (d, J=8.1 Hz, 1H), 7.11 (s, 1H), 6.24-6.16 (m, 1H), 5.31 (d, J=3.0 Hz, 2H), 4.99 (dt, J=25.9, 4.2 Hz, 4H), 4.82-4.63 (m, 3H), 4.57 (dd, J=5.9, 3.2 Hz, 4H), 4.52-4.40 (m, 4H), 4.34 (q, J=7.7, 6.7 Hz, 2H), 4.27-4.17 (m, 2H), 4.00 (d, J=6.1 Hz, 6H), 3.79 (t, J=5.4 Hz, 5H), 3.63 (dd, J=10.1, 6.7 Hz, 3H), 3.57-3.41 (m, 14H), 3.27 (q, J=6.2 Hz, 2H), 3.20 (s, 6H), 2.99 (s, 2H), 2.85 (q, J=7.4 Hz, 2H), 2.21 (d, J=3.3 Hz, 2H), 1.84 (s, 2H), 1.57 (d, J=6.4 Hz, 3H), 1.25 (d, J=6.5 Hz, 4H), 1.05 (d, J=6.1 Hz, 6H). MS-ESI+, observed MH+1312.4641: calculated MH+1312.4633.

Figure 8:
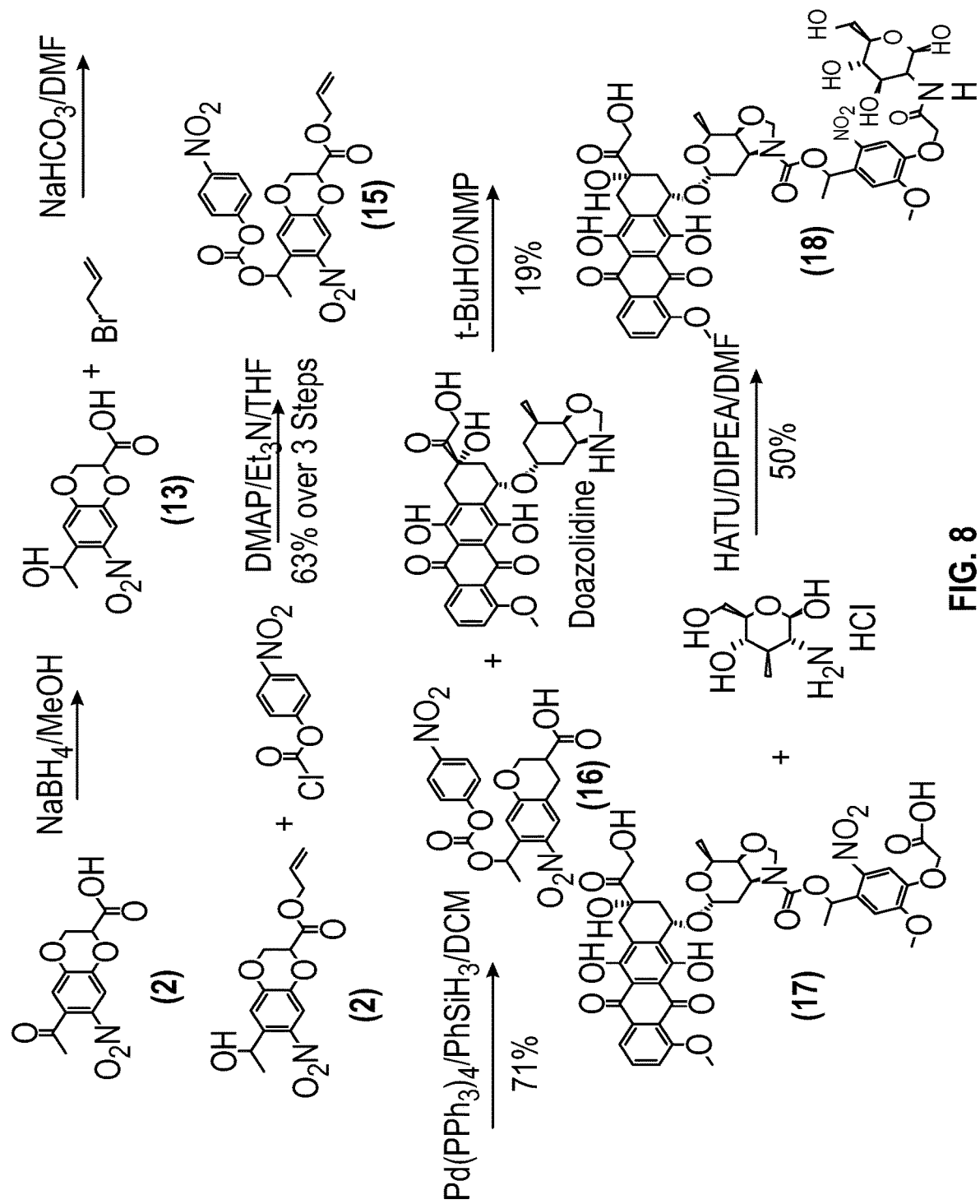
FIG. 8 shows the chemical synthesis scheme for glucose-photodoxazolidine.

Example 6: Synthesis of Glucose-photodoxazolidine (FIG. 8)

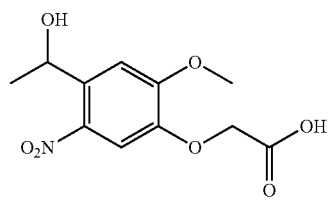 [SMILES: COc1cc(C(C)O)c([N+](=O)[O-])cc1OCC(=O)O]

Compound 13:

Compound 2 (0.119 g, 0.442 mmol) was dissolved in MeOH (10 mL) at 0° C. Sodium borohydride (0.0669 g, 1.768 mmol) was added slowly. The reaction mixture was stirred at 0° C. for 30 min and then allowed to warm to room temperature. The mixture was left at room temperature for 4 h. Since TLC showed the presence of the starting material, additional sodium borohydride (0.0669 g, 1.768 mmol) was added to the reaction at 0° C. The resulting mixture was stirred at room temperature for additional 1.5 hr. The reaction was quenched by adding saturated ammonium chloride solution. The mixture was acidified with 5% HCl solution and extracted with ethyl acetate. The combined organic layer was washed by brine, dried with sodium sulfate and rotary evaporated. The crude mixture was used for the next step without further purification. 1H NMR (400 MHz, Methanol-d4) δ 7.57 (s, 1H), 7.43 (s, 1H), 5.49-5.43 (m, 1H), 4.74 (s, 2H), 3.98 (s, 3H), 1.47 (d, J=6.3 Hz, 3H).

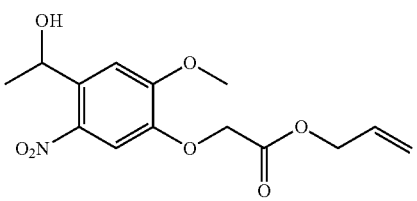 [SMILES: C=CCOC(=O)COc1cc([N+](=O)[O-])c(C(C)O)cc1OC]

Compound 14:

Compound 13 (0.12 g, 0.442 mmol) and sodium bicarbonate (0.074 g, 0.884 mmol) were dissolved in DMF (10 mL). The mixture was stirred at room temperature for 1 h. Then allyl bromide (0.080 g, 57.2 μL, 0.633 mmol) was added. The resulting mixture was stirred at room temperature overnight. Water was poured into the reaction, followed by extraction with ethyl acetate. The combined organic layer was washed with brine, dried with sodium sulfate and rotary evaporated. The crude mixture containing mostly compound 14 was used for the next step without further purification. 1H NMR (400 MHz, Chloroform-d) δ 7.53 (s, 1H), 7.36 (s, 1H), 5.93 (ddt, J=17.2, 10.4, 5.9 Hz, 1H), 5.58 (q, J=6.3 Hz, 1H), 5.41-5.26 (m, 2H), 4.78 (s, 2H), 4.71 (dt, J=5.8, 1.3 Hz, 2H), 4.04-3.99 (s, 3H), 1.56 (d, J=6.3 Hz, 3H).

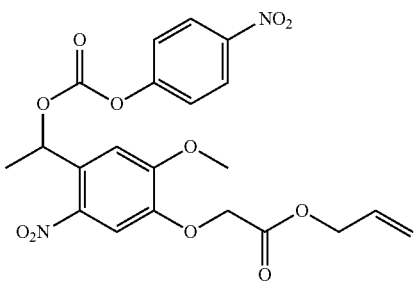 [SMILES: C=CCOC(=O)COc1cc([N+](=O)[O-])c(C(C)OC(=O)Oc2ccc([N+](=O)[O-])cc2)cc1OC]

Compound 15:

4-Nitrophenyl chloroformate (0.0761 g, 0.378 mmol), DMAP (0.0038 g, 0.0315 mmol) and triethyl amine (0.0637 g, 87.8 µL, 0.63 mmol) were dissolved in THF (2 mL) with molecular sieves (4 Å). After the mixture was stirred at room temperature for 5 min, compound 14 (0.098 g, 0.315 mmol) in THF (2 mL) was added. The resulting mixture was stirred at room temperature overnight. Ethyl acetate was added to the reaction, followed by washing with water, saturated sodium bicarbonate, and brine, and drying with sodium sulfate. The crude mixture was purified by silica gel column chromatography to yield 0.095 g (63% over 3 steps) of compound 15 as a solid. 1H NMR (400 MHz, Chloroform-d) δ 8.30-8.23 (m, 2H), 7.55 (s, 1H), 7.39-7.32 (m, 2H), 7.16 (s, 1H), 6.59-6.51 (m, 1H), 5.93 (ddt, J=17.2, 10.4, 5.9 Hz, 1H), 5.41-5.27 (m, 2H), 4.80 (s, 2H), 4.76-4.69 (m, 2H), 4.03 (s, 3H), 1.78 (d, J=6.4 Hz, 3H).

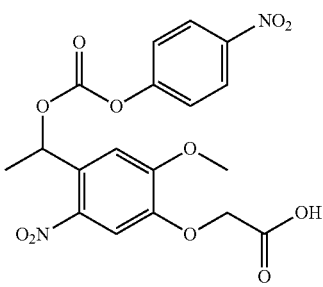 [SMILES: COc1cc(C(C)OC(=O)Oc2ccc([N+](=O)[O-])cc2)c([N+](=O)[O-])cc1OCC(=O)O]

Compound 16:

Compound 15 (0.048 g, 0.101 mmol), palladium (0) tetrakis (triphenyl phosphine) (0.0116 g, 0.010 mmol) and phenyl silane (0.109 g, 124.28 µL) were combined and dissolved in DCM. The reaction was carried out under an inert atomosphere at room temperature for 1 h. Ethyl acetate was added to the reaction, followed by washing with a solution of HCl in water (pH=3.5) and brine, and drying with sodium sulfate. The crude mixture was purified by silica gel column chromatography to yield 0.031 g (71%) of compound 16 as a solid. 1H NMR (400 MHz, Chloroform-d) δ 8.24 (d, J=8.9 Hz, 2H), 7.63-7.50 (m, 1H), 7.41-7.28 (m, 2H), 7.15 (s, 1H), 6.51 (d, J=5.7 Hz, 1H), 4.74 (s, 2H), 4.01 (s, 3H), 1.76 (d, J=6.4 Hz, 3H).

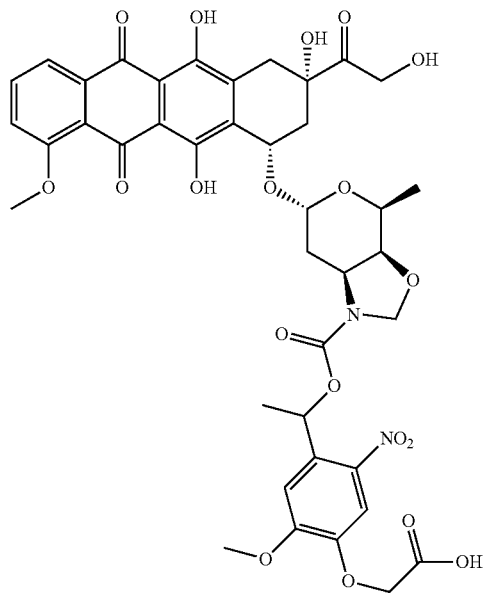 [SMILES: COc1cc(C(C)OC(=O)N2CO[C@@H]3[C@H](C)O[C@@H](O[C@H]4C[C@](O)(C(=O)CO)Cc5c(O)c6c(c(O)c54)C(=O)c4c(OC)cccc4C6=O)C[C@@H]32)c([N+](=O)[O-])cc1OCC(=O)O]

Compound 17:

Compound 16 (0.0157 g, 0.036 mmol) and HOBt (0.0073 g, 0.054 mmol) were combined and dissolved in NMP (2 mL). After the mixture was stirred at room temperature for 15 min, it was added to a solution of doxazolidine (0.02 g, 0.036 mmol) in NMP (2 mL). The resulting mixture was stirred at room temperature overnight. After DCM was added to the reaction mixture, it was washed with water and brine and dried over sodium sulfate. The crude mixture was purified by preparative RP-HPLC to yield 6.79 µmol (19%) of compound 17 as a red solid. 1H NMR (400 MHz, Chloroform-d) δ 13.80 (s, 1H), 13.22 (d, J=10.4 Hz, 1H), 8.00 (dd, J=11.8, 7.7 Hz, 1H), 7.83-7.69 (m, 1H), 7.61 (d, J=33.4 Hz, 1H), 7.37 (dd, J=13.3, 8.5 Hz, 1H), 7.00 (d, J=4.8 Hz, 1H), 6.50-6.35 (m, 1H), 5.44 (s, 1H), 5.26 (d, J=27.4 Hz, 2H), 5.13 (s, 1H), 5.09-4.93 (m, 2H), 4.84 (s, 1H), 4.74 (d, J=2.8 Hz, 3H), 4.69 (s, 2H), 4.13 (s, 3H), 4.06 (d, J=5.5 Hz, 5H), 3.94 (d, J=34.6 Hz, 4H), 3.26 (d, J=19.0 Hz, 2H), 3.03 (dd, J=18.9, 5.5 Hz, 1H), 2.44 (d, J=14.9 Hz, 1H), 2.35 (s, 1H), 2.23 (s, 1H), 2.18-2.06 (m, 1H), 1.79 (d, J=14.8 Hz, 1H), 1.66 (d, J=6.5 Hz, 4H), 1.37 (dd, J=6.5, 3.3 Hz, 4H). MS-ESF, observed MH⁻ 851.2132: calculated 851.2147.

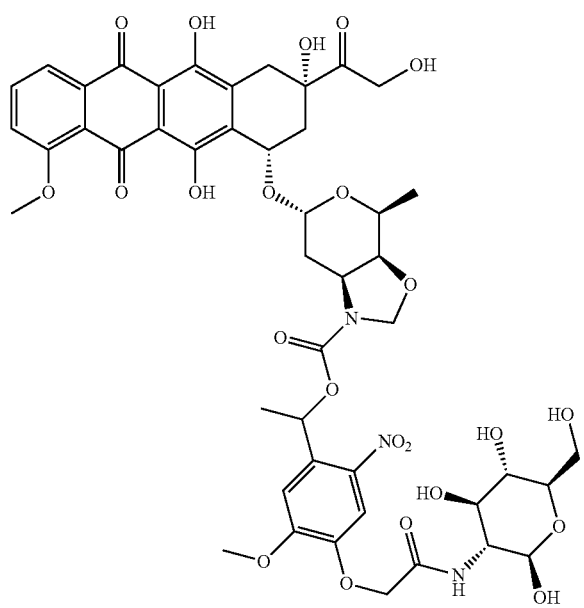 [SMILES: COc1cc(C(C)OC(=O)N2CO[C@@H]3[C@H](C)O[C@@H](O[C@H]4C[C@](O)(C(=O)CO)Cc5c(O)c6c(c(O)c54)C(=O)c4c(OC)cccc4C6=O)C[C@@H]32)c([N+](=O)[O-])cc1OCC(=O)N[C@@H]1[C@@H](O)[C@H](O)[C@@H](CO)O[C@H]1O]

Compound 18 (Glucose-Photodoxazolidine):

Compound 17 (0.00655 g, 0.00769 mmol), D-glucosamine·HCl (0.00248 g, 0.0115 mmol) and HATU (0.0044 g, 0.0115 mmol) were combined and dissolved in DMF (2 mL). Then DIPEA (0.00298 g, 0.004 mL, 0.023 mmol) was added. The resulting mixture was stirred at room temperature for 1 h. Water was poured into the reaction and the mixture was extracted with a solution of DCM:isopropanol=3:1. The combined organic layer was dried over sodium sulfate and the solvent rotary evaporated. The crude mixture was purified by preparative RP-HPLC to yield 3.84 μmol (50%) of glucose-photodoxazolidine (compound 18) as a red solid. 1H NMR (400 MHz, DMSO-d6) δ 7.88 (d, J=17.0 Hz, 1H), 7.44 (dd, J=8.6, 2.7 Hz, 1H), 7.07 (s, 1H), 6.40 (s, 1H), 6.16 (d, J=6.4 Hz, 1H), 5.26 (s, 2H), 4.96 (d, J=18.2 Hz, 5H), 4.76 (s, 2H), 4.65 (s, 3H), 4.58 (s, 3H), 4.53 (t, J=5.3 Hz, 5H), 4.39-4.17 (m, 3H), 3.96 (d, J=8.2 Hz, 12H), 3.69-3.53 (m, 5H), 3.53-3.40 (m, 3H), 2.95 (s, 2H), 2.17 (d, J=4.5 Hz, 3H), 1.80 (s, 1H), 1.53 (d, J=6.4 Hz, 5H), 1.23 (s, 3H). MS-ESI⁻, observed MH⁻ 1012.2896; calculated MH⁻ 1012.2835.

Example 7: Characterization of MARCKS-PEG-Photodoxazolidine, Glucose-PEG-Photodoxazolidine, and Glucose-Photodoxazolidine Cell Culture:

The breast carcinoma line MDA-MB-231 was cultured in Minimum Essential Media (MEM) supplemented with 10% of fetal bovine serum (FBS), 100 units/mL of penicillin and 100 μg/mL of streptomycin, and 1 mM of sodium pyruvate. The cells were incubated at 37° C. in an atmosphere of 95% air and 5% $CO_2$.

Tumor Cell Growth Inhibition:

The cells were seeded to 96-well plates at a density of 1000 cells/well and allowed to adhere overnight. The prodrugs with various concentrations in MEM were added and the cells were incubated at 37° C. for 24 h. After the media was removed, the cells were washed with PBS two times. The cells in PBS (50 μL) were irradiated for 15 min, followed by incubating at room temperature for 30 min. The PBS was replaced with fresh media and the cells were grown until the no-drug control reached 80% confluency, or 5 days. Cell density was measured by crystal violet staining.

The membrane permeability of the photoactivated prodrugs and their cellular uptake by MDA-MB-231 human breast cancer cells were each monitored by fluorescence microscopy. After the cells were grown with the prodrugs for 24 h, they were washed with PBS two times to remove the prodrugs that remained outside of the cells. The cellular uptake of 10 μM glucose-photodoxazolidine and glucose-PEG-photodoxazolidine was monitored with the fluorescence of the anthraquinone fluorophore. The prodrugs were then activated inside of the cells by black lamp UV irradiation (maximum intensity at 350 nm) for 15 min. IC50 assays (shown in Table 5) showed that the cytotoxicities increased about three-fold upon UV irradiation. MARCKS-PEG-photodoxazolidine including the MARCKS-ED peptide (SEQ ID NO:1) showed an IC50 of 7.9 μM for MDA-MB-231 cells, which is approximately 165-fold more toxic than the prodrug without UV irradiation (Table 5). This drastic change of cytotoxicity presumably arises from membrane permeability of MARCKS-ED peptide and possibly some phototoxicity from longer irradiation time.

TABLE 5

IC50 (nM) values of the targeted photodoxazolidine prodrugs on MDA-MD-231, human breast cancer cells.

| Light Control | Glucose-PEG-Photodoxazolidine | Glucose-Phtodoxazolidine | MARCKS-PEG-Photodoxazolidine |
|---|---|---|---|
| + | 750 | 832 | 7.9 |
| − | 2400 | 2080 | 1300 |

The foregoing examples of the present invention have been presented for purposes of illustration and description. Furthermore, these examples are not intended to limit the invention to the form disclosed herein. Consequently, variations and modifications commensurate with the teachings of the description of the disclosure, and the skill or knowledge of the relevant art, are within the scope of the present invention. The specific embodiments described in the examples provided herein are intended to further explain the best mode known for practicing the invention and to enable others skilled in the art to utilize the invention in such, or other, embodiments and with various modifications required by the particular applications or uses of the present invention. It is intended that the appended claims be construed to include alternative embodiments to the extent permitted by the prior art.

What is claimed is:
1. A compound having a chemical structure selected from the group consisting of:
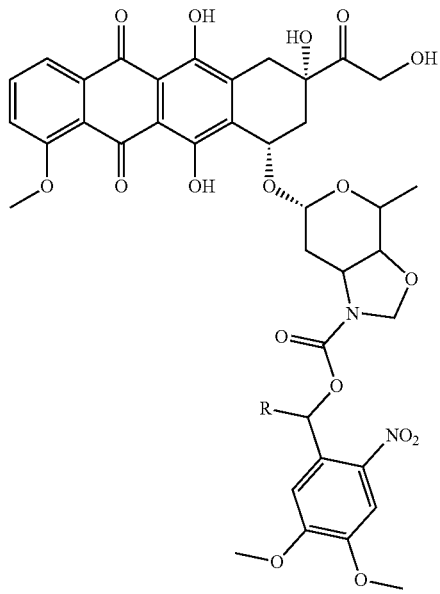
wherein R is H or CH$_3$,
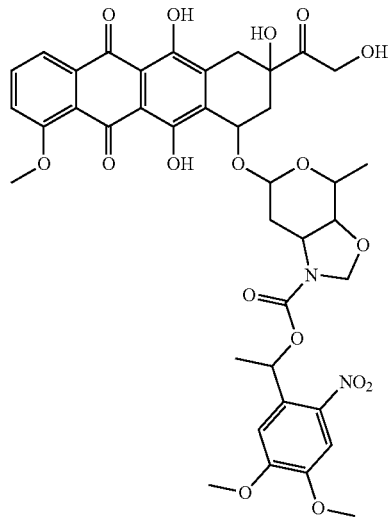
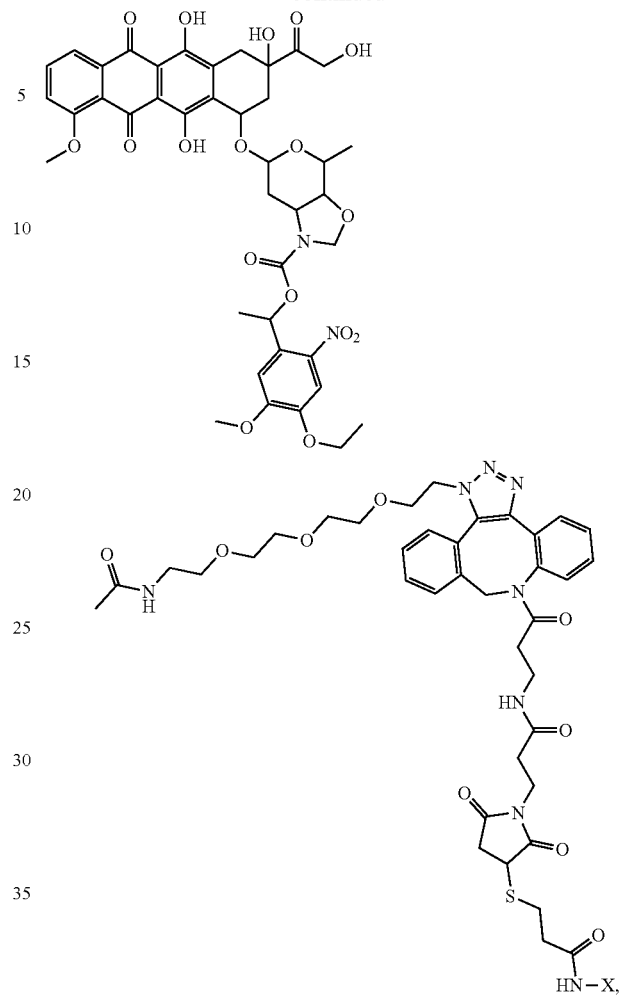
wherein X is a peptide having a sequence from the group consisiting of:
KKKKKRFSFKKSFKLSGFSFKKNKK (SEQ ID NO: 1),
KKKKKRFSFKK (SEQ ID NO: 2),
SFKLSGFSFKKNKK (SEQ ID NO: 3),
RRRRRRRRR (SEQ ID NO: 4),
KKKKKKKKK (SEQ ID NO: 5),
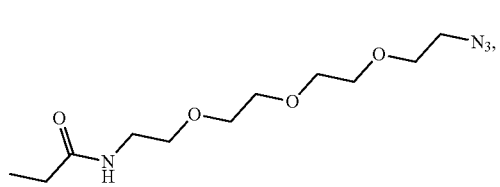
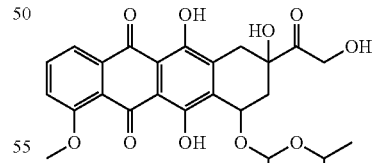
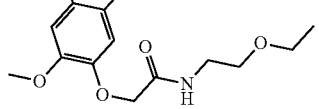

-continued

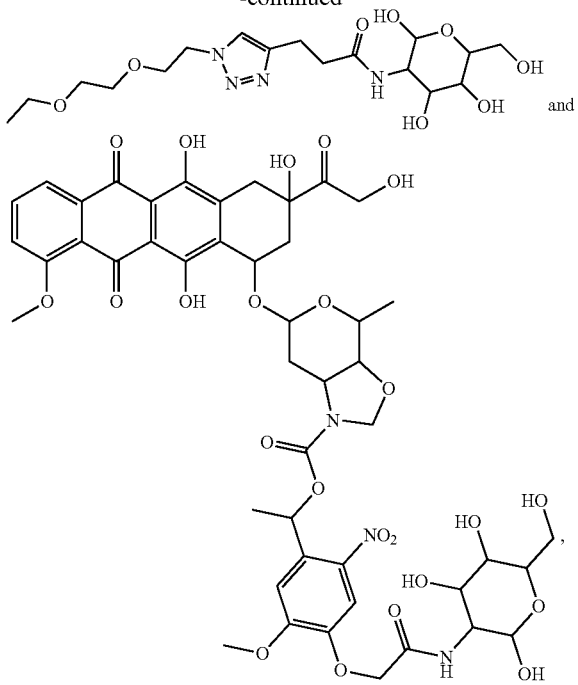

and and pharmaceutically-acceptable salts thereof.

2. A pharmaceutical composition comprising a compound of claim 1, and at least one excipient.

3. The pharmaceutical composition of claim 2, further comprising wherein the composition is formulated for parenteral administration.

4. The pharmaceutical composition of claim 2, further comprising wherein the composition is formulated for oral administration.

5. A method of treating cancer, comprising the step of administering an effective amount of at least one compound of claim 1 to a subject in need thereof and further photo-activating said at least one compound of claim 1 wherein the cancer is selected from the group consisting of ovarian cancer and breast cancer.

6. The method of claim 5, wherein the at least one compound of claim 1 is co-administered with at least one of the following: 18-F-deoxyglucose (18-FDG), UV light, a PET scan, and Cherenkov radiation.

* * * * *

SEQUENCE LISTING

<160> NUMBER OF SEQ ID NOS: 5

<210> SEQ ID NO 1
<211> LENGTH: 25

```
<212> TYPE: PRT
<213> ORGANISM: Artificial Sequence
<220> FEATURE:
<223> OTHER INFORMATION: Synthetic Peptide

<400> SEQUENCE: 1

Lys Lys Lys Lys Lys Arg Phe Ser Phe Lys Lys Ser Phe Lys Leu Ser
1               5                   10                  15

Gly Phe Ser Phe Lys Lys Asn Lys Lys
            20                  25

<210> SEQ ID NO 2
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 2

Lys Lys Lys Lys Lys Arg Phe Ser Phe Lys Lys
1               5                   10

<210> SEQ ID NO 3
<211> LENGTH: 14
<212> TYPE: PRT
<213> ORGANISM: Artificial Sequence
<220> FEATURE:
<223> OTHER INFORMATION: Synthetic Peptide

<400> SEQUENCE: 3

Ser Phe Lys Leu Ser Gly Phe Ser Phe Lys Lys Asn Lys Lys
1               5                   10

<210> SEQ ID NO 4
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 4

Arg Arg Arg Arg Arg Arg Arg Arg Arg
1               5                   10

<210> SEQ ID NO 5
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 5

Lys Lys Lys Lys Lys Lys Lys Lys Lys Lys
1               5                   10
```